US011591655B2

(12) United States Patent
Hare et al.

(10) Patent No.: US 11,591,655 B2
(45) Date of Patent: Feb. 28, 2023

(54) DIAGNOSTIC TRANSCRIPTOMIC BIOMARKERS IN INFLAMMATORY CARDIOMYOPATHIES

(71) Applicant: UNIVERSITY OF MIAMI, Miami, FL (US)

(72) Inventors: Joshua Hare, Miami Beach, FL (US); Bettina Heidecker, Miami, FL (US)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 15/860,175

(22) Filed: Jan. 2, 2018

(65) Prior Publication Data

US 2018/0251843 A1    Sep. 6, 2018

Related U.S. Application Data

(63) Continuation of application No. 13/376,046, filed as application No. PCT/US2010/037018 on Jun. 2, 2010, now abandoned.

(60) Provisional application No. 61/183,306, filed on Jun. 2, 2009.

(51) Int. Cl.
  *C12Q 1/6883* (2018.01)

(52) U.S. Cl.
  CPC ...... *C12Q 1/6883* (2013.01); *C12Q 2600/112* (2013.01); *C12Q 2600/136* (2013.01); *C12Q 2600/158* (2013.01)

(58) Field of Classification Search
  CPC ............ C12Q 1/6883; C12Q 2600/112; C12Q 2600/158
  See application file for complete search history.

(56) References Cited

U.S. PATENT DOCUMENTS

| | | |
|---|---|---|
| 4,016,043 A | 4/1977 | Schuurs et al. |
| 4,018,653 A | 4/1977 | Mennen |
| 4,424,279 A | 1/1984 | Bohn et al. |
| 4,683,202 A | 7/1987 | Mullis |
| 4,843,155 A | 6/1989 | Chomczynski |
| 5,030,015 A | 7/1991 | Baker et al. |
| 5,445,934 A | 8/1995 | Fodor et al. |
| 5,445,935 A | 8/1995 | Royer |
| 5,700,637 A | 12/1997 | Southern |
| 5,807,522 A | 9/1998 | Brown et al. |
| 5,854,033 A | 12/1998 | Lizardi |
| 2001/0051344 A1 | 12/2001 | Shalon et al. |
| 2003/0026793 A1 | 2/2003 | Guy |
| 2004/0132013 A1 | 7/2004 | De Bold |
| 2004/0167067 A1 | 8/2004 | Griggs et al. |
| 2005/0143628 A1 | 6/2005 | Dai et al. |
| 2005/0196764 A1 | 9/2005 | Liew |
| 2006/0094038 A1 | 5/2006 | Wagner et al. |
| 2006/0172311 A1 | 8/2006 | Cohen et al. |
| 2006/0246495 A1 | 11/2006 | Garrett et al. |
| 2007/0031873 A1 | 2/2007 | Wang et al. |
| 2007/0292345 A1 | 12/2007 | Khowlton et al. |
| 2008/0305512 A1 | 12/2008 | Mattingly et al. |
| 2009/0215042 A1 | 8/2009 | Sella-Tavor et al. |
| 2010/0112587 A1 | 5/2010 | Hare et al. |
| 2010/0152055 A1 | 6/2010 | Kozono et al. |
| 2010/0190650 A1 | 7/2010 | Hare et al. |
| 2012/0142544 A1 | 6/2012 | Hare et al. |
| 2013/0203622 A1 | 8/2013 | Hare et al. |
| 2014/0329710 A1 | 11/2014 | Hare et al. |

FOREIGN PATENT DOCUMENTS

| | | |
|---|---|---|
| CA | 2553665 A1 | 2/2007 |
| EP | 1930426 A1 | 6/2008 |
| JP | 200749991 A | 3/2007 |
| WO | 2001075166 A2 | 10/2001 |
| WO | 2006084272 A2 | 8/2006 |
| WO | 2007026896 A1 | 3/2007 |
| WO | 2008137586 A1 | 11/2008 |
| WO | 2008137595 A1 | 11/2008 |
| WO | 2010141546 A1 | 12/2010 |

OTHER PUBLICATIONS

Ruppert et al. (2012) Molecular signatures and the study of gene expression profiles in inflammatory heart diseases. Herz, 37:619-626 (Year: 2012).*
Slonim, D., (2002) From patterns to pathways: gene expression data analysis comes of age. Nature Genetics Supplement, 32:502-508 (Year: 2002).*
Hosmer et al. (1991) The Importance of Assessing the Fit of Logistic Regression Models: A Case Study. American Journal of Public Health, 81(12):1630-1635 (Year: 1991).*
Hosmer et al., The importance of assessing the fit of logistic regression models: a case study. American Journal of Public Health (1991), 81(12):1630-1635 (Year: 1991).*
Ruppert et al. Molecular signatures and the study of gene expression profiles in inflammatory heart diseases (2012) Herz, 37:619-626 (Year: 2012).*
Dallas et al., Gene expression levels assessed by oligonucleotide microarray analysis and quantitative real-time RT-PCR—how well do they correlate? BMC Genomics (2005), 6(59):1-10 (Year: 2005).*
U.S. Appl. No. 15/632,926, filed Jun. 26, 2017, which is a continuation of U.S. Appl. No. 13/801,450, filed Mar. 13, 2013, which is a continuation of U.S. Appl. No. 12/609,194, filed Oct. 30, 2009, which is a continuation-in-part of International Application No. PCT/US2008/062290, filed May 1, 2008, which claims priority to U.S. Appl. No. 60/915,215, filed May 1, 2007.
U.S. Appl. No. 16/160,037, filed Oct. 15, 2018, which is a continuation of U.S. Appl. No. 14/334,024, filed Jul. 17, 2014, which is a continuation of U.S. Appl. No. 12/610,529, filed Nov. 2, 2009, which is a continuation-in-part of International Application No. PCT/US2008/062281, filed May 1, 2008, which claims priority to U.S. Appl. Nos. 61/019,749, filed Jan. 8, 2008; U.S. Appl. No. 60/915,215, filed May 1, 2007; and U.S. Appl. No. 60/915,224, filed May 1, 2007.

(Continued)

*Primary Examiner* — Lora E Barnhart Driscoll
*Assistant Examiner* — Catherine Konopka
(74) *Attorney, Agent, or Firm* — Buchanan Ingersoll & Rooney PC

(57) ABSTRACT

Molecular signatures that function as very sensitive diagnostic biomarker for myocarditis, heart disease and disorders thereof, are identified.

18 Claims, 5 Drawing Sheets

(56) References Cited

OTHER PUBLICATIONS

Maisel, "B-type natriuretic peptide levels: diagnostic and prognostic in congestive heart failure: what's next?" Circ. (2002), 105:2328-2331.
Margulies et al., "Mixed messages: transcription patterns in failing and recovering human myocardium," Circ Res (Feb. 2005), 96:592-599.
Mazhari et al., "Advances in cell-based therapy for structural heart disease," Prog Cardiovasc Dis (May/Jun. 2007), 49:387-395.
Moore et al., "Stem cells and their niches," Science (Mar. 2006), 311:1880-1885.
Mukherjee et al., "Estimating dataset size requirements for classifying DNA microarray data," Journal of Computational Biology (Nov. 2003), 10:119-142.
Negishi et al., "Identification and cDNA cloning of single-stranded DNA binding proteins that interact with the region upstream of the human c-myc gene," Oncogene (1994), 9:1133-1143.
Ota et al., "Complete sequencing and characterization of 21,243 full-length human cDNAs," Nature Genetics (Jan. 2004), 36:40-45.
Perou et al., "Molecular portraits of human breast tumours," Nature (Aug. 2000), 406:747-752.
Raeker et al., "Obscurin is required for the lateral alignment of striated myofibrils in Zebrafish," Develop. Dynamics (2006), 235:2018-2029.
Semenza, "Pulmonary vascular responses to chronic hypoxia mediated by hypoxia-inducible factor 1," Proc Am Thorac Soc (2005), 2:68-70.
Sharma et al., "DNA microarray analysis for human congenital heart disease," Cell Biochem. and Biophys. (2006), 44(1):1-9.
Singh et al., "Microarray-based comparison of three amplification methods for nanogram amounts of total RNA," Am J Physiol Cell Physiol (2005), 288:C1179-C1189.
Steenman et al., "Transcriptomal analysis of failing and nonfailing human hearts," Physiol Genomics (2003), 12:97-112.
Storey, "A direct approach to false discovery rates," Journal of the Royal Statistical Society (2002), 64:479-498.
Thomas, "Hybridization of denatured RNA and small DNA fragments transferred to nitrocellulose," Proc. Natl. Acad. Sci. USA (Sep. 1980), 77:5201-5205.
Tibshirani et al., "Diagnosis of multiple cancer types by shrunken centroids of gene expression," Proc Natl Acad Sci USA (May 2002), 99(10):6567-6572.
Tusher et al., "Significance analysis of microarrays applied to the ionizing radiation response," Proc Natl Acad Sci USA (Apr. 2001), 98(9):5116-121.
Van Haaften et al., "Biologically relevant effects of mRNA amplification on gene expression profiles," BMC Bioinformatics (2006), 7(200):1-15.
Azuaje et al., "Computational Biology for Cardiovascular Biomarker Discovery," Briefings in Bioinform. (2009), 10 (4):367-377.
Stec et al., "Comparison of the Predictive Accuracy of DNA Array-Based Multigene Classifiers across cDNA Arravys and Affymetrix GeneChips," J. Mol. Diagn. (Aug. 2005), 7(3):357-367.
Cheung et al., "Making and Reading Microarrays," Nature Genetics Suppl. (Jan. 1999) 21:15-19.
Huang et al., "A comparative study of discriminating human heart failure etiology using gene expression profiles," BMC Bioinform. (Aug. 24, 2005), Biomed Central, London, 6(205):1-15.
International Search Report dated Aug. 6, 2008 for corresponding application PCT/US2008/062281.
International Search Report dated Jul. 30, 2008 for corresponding application PCT/US2008/062290.
International Search Report dated Sep. 21, 2010 for corresponding application PCT/US2010/037018.
Kim et al., "Effects of sample size on robustness and prediction accuracy of a prognostic gene signal," BMC Bioinform. (May 16, 2009), 10(147):1-10.
Lockart, Expression monitoring by hybridization to high-density oligonucleotide arrays, Nature Biotech. (Dec. 1996) 14(13):1675-1680 (abstract).
Harper, "Can sensitivity and specificity estimates from research studies be made more meaningful for clinincal practice?" Opthal. Physiol. Opt. (2002), 22:271-273.
Rudy et al., "Differential function of CD80- and CD86-transfected human melanoma cells in the presence of IL-12 and IFN-gamma," Int. Immunol. (1997), 9(6):853-860.
Franz et al., "Serum troponin T: diagnostic marker for acute myocarditis," Clin. Chem. (1996), 42(2):340-341.
Davies et al., ABC of Heart Failure; Management: diuretics, ACE inbhibitors, and nitrates, BMJ 320:428-320 (Feb. 12, 2000).
Kittleson et al., Molecular signature analysis: the potential of gene-expression analysis in cardiomyopathy, Future Cardiol. (2005), 1(6):793-808.
Japanese Office Action dated Apr. 2, 2013 for corresponding application JP Application No. 2010-506649.
Kroese et al "Genetic tests and their evaluation: Can we answer the key questions?" (2004) Genetics in Medicine 6 (6) :475-480.
Lucentini "Gene Association Studies Typically Wrong" The Scientist, (2004) 18(24):20.
Tang et al. (Cellular and Molecular Biology Letters, 2007. vol. 12, pp. 176-191).
Watanabe et al. (Translational Research, 2008. vol. 152, No. 3, pp. 119-127).
Heidecker et al. Transcriptomic Biomarkers for the Accurate Diagnosis of Myocarditis (2011) vol. 123, pp. 1174-1184.
Database Gene Expression Omnibus NCBI (2003) Affymetrix Human Genome U133 Pius 2.0 Array.
Heidecker, B. et al. (2007) "The use of transcriptomic biomarkers for personalized medicine," Heart Fall. Rev., 12:1-11.
Nanni, L. et al. (2006) "Differential gene expression profiling in genetic and multifactorial cardiovascular diseases," Journal of Molecular and Cellular Cardiology, 41: 934-948.
Written Opinion of the International Searching Authority (US) for International Application No. PCT/US08/62290, opinion completed Jul. 30, 2008.
Morgun et al., "Molecular Profiling Improves Diagnoses of Rejection and Infection in Transplanted Organs," Circ. Res. (Jun. 23, 2006), 98(12):e74-83.
European Office Action dated Feb. 17, 2014 for corresponding EP 08754986.1.
Australia Office Action dated Feb. 8, 2013 for corresponding AU2008247658.
European Office Action dated Apr. 11, 2013 for corresponding EP 08754986.1.
Japanese Office Action dated Mar. 26, 2013 for corresponding JP 2010-506653 (untranslated).
Grzeskowiak et al., "Expression profiling of human idiopathic dilated cardiomyopathy," Cardiovascular Res. (2003), 59:400-411.
Heidecker et al., "Transcriptomic Biomarkers for Individual Risk Assessment in New-Onset Heart Failure," Circ. (2008), 118:238-246.
Kittleson et al., "Gene expression analysis of ischemic and nonischemic cardiomyopathy: shared and distinct genes in the development of heart failure," Physiol. Genomics (2005), 21:299-307.
Kittleson et al., "Gene expression in giant cell myocarditis: Altered expression of immune response genes," Int'l J. Cardio. (2005), 102:333-340.
Kittleson et al., "Identification of a Gene Expression Profile That Differentiates Between Ischemic and Nonischemic Cardiomyopathy" Circ. (2004), 110(22):3444-3451.
McManus et al., "Genetic Determinants of Coxsackievirus B3 Pathogenesis" Ann. N.Y. Acad. Sci. (2002), 975:169-179.
Yanagawa et al., "Affymetrix Oligonucleotide Analysis of Gene Expression in the Injured Heart," Methods in Mol. Med. (2005), 112:305-320.
Japanese Office Action dated Mar. 4, 2014 for corresponding application JP Application No. 2010-506649.
International Search Report dated Aug. 6, 2008 for corresponding application WO 2008/137586 A1.

(56) References Cited

OTHER PUBLICATIONS

European Supplemental Search Report dated Sep. 15, 2010 for corresponding application EP 08747396.
Archacki et al., "Expression profiling of cardiovascular disease," Human Genomics, (Apr. 2004) 1(5):355-370.
Archacki et al., "Identification of new genes differentially expressed in coronary artery disease by expression profiling," Physiological Genomics, (Sep. 2003), 15(1):65-74.
Barth et al., "The Potential for the Transcriptome to Serve as a Clinical Biomarker for Cardiovascular Diseases," Circ. Res. (2006) 98:1459-61.
Boyle et al., "Is stem cell therapy ready for patients? Stem Cell Therapy for Cardia Repair. Ready for the Next Step." Circulation (2006) 114:339-352.
Chakravarti et al., "Nature, nurture and human disease," Nature (2003), 421:412-4.
Chen et al., "Expression of ssDNA in mammalian cells," BioTechniques (Jan. 2003), 34(1):167-171.
Cooper et al., "The role of endomyocardial biopsy in the management of cardiovascular disease: a scientific statement from the American Heart Association, the American College of Cardiology, and the European Society of Cardiology", Circulation (2007), 116:2216-2233.
Dafforn et al., "Linear mRNA amplification from as little as 5 ng total RNA for global gene expression analysis," Biotechniques (Nov. 2004), 37:854-857.
Deng et al., "Noninvasive discrimination of rejection in cardiac allograft recipients using gene expression profiling," American Journal of Transplantation (2006), 6:150-160.
Depre et al., "Unloaded heart in vivo replicates fetal gene expression of cardiac hypertrophy," Nature Medicine (Nov. 1998), 4:1269-1275.
Diaz et al., "Prediction of outcome in dilated cardiomyopathy," Br Heart (1987), 58:393-399.
Felker et al., "The problem of decompensated heart failure: nomenclature, classification, and risk stratification," Am Heart J (Feb. 2003), 145:S18-S25.
Felker et al., "Underlying causes and long-term survival in patients with initially unexplained cardiomyopathy," N Engl J Med (Apr. 2000) 342:1077-1084.
Geisler et al., "Obscurin-like 1, OBSL1, is a novel cytoskeletal protein related to obscurin," Genomics (Apr. 2007), 89:521-531.
Guatelli et al., "Isothermal, in vitro amplification of nucleic acids by a multienzyme reaction modeled after retroviral replication," Proc. Natl. Acad. Sci. USA, (Mar. 1990) 87:1874-1878.
Hajjar et al, "Prospects for gene therapy for heart failure," Circ Res (2000), 6:616-621.
Hall et al., "Molecular signature of recovery following combination left ventricular assist device (LVAD) support and pharmacologic therapy," Eur. Heart J. (2007), 28:613-627.

Hare, "The dilated, restrictive and infiltrative cardiomyopathies," In: Zipes DP, Libby P, Bonow R, Braunwald E, editor, Braunwald's Heart Disease. 8 ed. Elsevier; 2007, 1739-1762.
Heidbreder et al, "Hypoxia rapidly activates HIF-3alpha mRNA expression," FASEB J (Jun. 2003), 17:1541-1543.
Ito et al., "A novel WD40 repeat protein, WDC146, highly expressed during spermatogenesis in a stage-specific manner," Biochem Biophys Res Commun (2001) ;280:656-663.
Kittleson et al., "Increased levels of uric acid predict haemodynamic compromise in patients with heart failure independently of B-type natriuretic peptide levels," Heart (2007),93:365-367.
Kwoh et al., "Transcription-based amplification system and detection of amplified human immunodeficiency virus type 1 with a bead-based sandwich hybridization format," Proc. Natl. Acad. Sci. USA, (Feb. 1989), 86:1173-1177.
Liew et al., "The peripheral blood transcriptome dynamically reflects system wide biology: a potential diagnostic tool," J. Lab. Clin. Med. (2006), 147:126-132.
Lowes et al., "Serial Gene Expression Profiling in the Intact Human Heart," J. Heart Lung Transplant (May 2006), 25(5):579-588.
Lowes et al., Myocardial gene expression in dilated cardiomyopathy treated with beta-blocking agents, N Engl J Med (May 2002), 346(18):1357-1365.
Luo et al., "Disruption of mRad50 causes embryonic stem cell lethality, abnormal embryonic development, and sensitivity to ionizing radiation," Proc Natl Acad Sci USA (Jun. 1999), 96:7376-7381.
Notice of Allowance dated Jul. 5, 2018 received in U.S. Appl. No. 14/334,024.
Non-final Office Action dated Jan. 18, 2019 in U.S. Appl. No. 15/632,926.
Non-final Office Action dated Apr. 7, 2015 in U.S. Appl. No. 13/376,046.
Final Office Action dated Dec. 1, 2016 in U.S. Appl. No. 13/376,046.
Non-final Office Action dated Sep. 15, 2015 in U.S. Appl. No. 13/801,450.
Final Office Action dated 05-25-20116 in U.S. Appl. No. 13/801,450.
Final Office Action dated Sep. 13, 2012 in U.S. Appl. No. 12/609,194.
Non-final Office Action dated Jan. 12, 2012 in U.S. Appl. No. 12/609,194.
"Affymetrix Human Genome U133 Plus 2.0 Array," Accession GPL570, GEO Expression; Nov. 7, 2003.
Non-final Office Action dated Jan. 17, 2014 in U.S. Appl. No. 12/610,529.
Non-final Office Action dated May 14, 2013 in U.S. Appl. No. 12/610,529.
Non-final Office Action dated Jul. 26, 2012 in U.S. Appl. No. 12/610,529.
Final Office Action dated Dec. 6, 2017 in U.S. Appl. No. 14/334,024.
Non-final Office Action dated Mar. 27, 2017 in U.S. Appl. No. 14/334,024.
Non-final Office Action dated Jul. 14, 2016 in U.S. Appl. No. 14/334,024.

* cited by examiner

DIAGNOSTIC TRANSCRIPTOMIC BIOMARKERS IN INFLAMMATORY CARDIOMYOPATHIES

CROSS-REFERENCE TO RELATED APPLICATIONS

This application is a continuation of U.S. application Ser. No. 13/376,046, filed Feb. 24, 2012, which is a national stage entry of International Application No. PCT/US10/37018, filed Jun. 2, 2010, which claims priority to U.S. Provisional Application No. 61/183,306, filed Jun. 2, 2009, all of which are incorporated herein by reference in their entirety.

STATEMENT REGARDING FEDERALLY SPONSORED RESEARCH

This invention was made with U.S. government support under grant numbers U54-HL081028 (Specialized Center for Cell Based Therapy) and R01s HL084275, AG025017, HL065455, and HL094849, which were awarded by the National Institutes of Health. The U.S. government may have certain rights in the invention.

FIELD OF THE INVENTION

This invention relates to biomarkers of heart disease, myocarditis, novel drug therapeutic targets, compositions and methods of predicting, diagnosing and treating heart diseases and related disorders thereof. More specifically, the invention concerns methods and compositions based on unique molecular signatures associated with various aspects of cardiac diseases and disorders.

BACKGROUND

The myocardites are inflammatory diseases of the heart that have variable clinical presentations and are caused by a range of underlying inflammatory variants. Of new onset heart failure, 10-30% may be caused by cardiac inflammation, and viral infection systemic or local inflammatory diseases, or genetic predisposition represent inciting factors. Myocarditis can be difficult to diagnose requiring multiple endomyocardial biopsies (EMBs). Even with multiple biopsies, consensus among pathologists has been difficult to attain. Inaccurate or uncertain diagnosis is of major concern, since emerging therapies specifically targeting inflammatory or viral heart disease, have the potential to reverse the disease process. In a previous decision analysis investigating the value of EMBs to improve clinical outcome with specific therapy, histological inaccuracy was a major limiting factor for efficacy of treatment. In addition, the important subtypes of myocarditis have highly distinct outcomes, require markedly different therapeutic strategies, and can be difficult to distinguish based on standard histopathology. Current attempts to improve diagnostic accuracy include screening for viral RNA in endomyocardial biopsies, serum anti-heart autoantibodies, and use of magnetic resonance imaging (MRI).

SUMMARY

Molecular signatures that function as very sensitive diagnostic biomarker for myocarditis, cardiovascular diseases and disorders, heart disease and disorders thereof, were identified. The biomarkers also distinguish between various cardiac diseases and disorders allowing for accurate diagnosis. In addition the biomarkers provide for the identification of individuals at risk of developing cardiac diseases and disorders. The transcriptomic biomarkers provide for the early diagnosis of cardiovascular diseases or disorders.

Transcriptomic biomarker s (TBBs) were identified to distinguish or differentially diagnose between giant cell myocarditis and cardiac sarcoidosis; peripartum cardiomyopathy and lymphocytic cardiomyopathy; myocarditis and idiopathic dilated cardiomyopathy; cardiac sarcoidosis, giant cell myocarditis, peripartum cardiomyopathy, and systemic lupus erythematosus with cardiac involvement. The biomarkers or marker signatures comprised molecules some of which were up-regulated, down-regulated, no change, absent, etc (i.e., differentially expressed) as compared to normal healthy controls. The signatures not only allow for the early diagnosis and diagnostic differentiation between various diseases and disorders but also for identifying individuals at risk for one or more cardiovascular diseases or disorders.

Other aspects of the invention are described infra.

DETAILED DESCRIPTION

Figure 1:
FIG. 1 shows: Significance Analysis of Microarrays Plot of differentially expressed genes in lymphcytic myocarditis vs idiopathic dilated cardiomyopathy: There were 9,878 genes differentially expressed in myocardits (n=16) vs IDCM (n=32; q<5%, fold change>1.2), of which 2,313 were overexpressed (depicted in red) and 7,565 were downregulated (depicted in green).

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions

In accordance with the present invention and as used herein, the following terms are defined with the following meanings, unless explicitly stated otherwise.

As used herein, "a", "an," and "the" include plural references unless the context clearly dictates otherwise.

As used herein, a "molecular signature" or "signature" or "biomarker" or "transcriptomic based biomarker" are used interchangeably herein and refers to the biomolecules identified in Tables 1 to 19. Thus, Table 1 comprising the biomolecules listed therein, represents one biomarker or molecular signature; Table 2 comprising the biomolecules listed therein, represents another one biomarker or molecular signature; and so forth. As more biomolecules are discovered, each newly identified biomolecules can be assigned to any one or more biomarker or molecular signature. Each biomolecule can also be removed, reassigned or reallocated to a molecular signature. Thus, in some embodiments the molecular signature comprises at least ten biomolecules. The ten biomolecules are selected from the genes identified herein, or from newly identified biomolecules. Any one of the signatures can be used in the diagnosis of a disease or disorder, for example, myocarditis and idiopathic cardiomyopathy or differentiate between myocarditis and idiopathic cardiomyopathy. Mammalian sequences are preferred, with human sequences the most preferred.

The term "biomolecule" refers to DNA, RNA (including mRNA, rRNA, tRNA and tmRNA), nucleotides, nucleosides, analogs, polynucleotides, peptides and any combinations thereof.

A base "position" as used herein refers to the location of a given base or nucleotide residue within a nucleic acid.

As used herein, the term "array" refers to an ordered spatial arrangement, particularly an arrangement of immobilized biomolecules.

As used herein, the term "addressable array" refers to an array wherein the individual elements have precisely defined x and y coordinates, so that a given element at a particular position in the array can be identified.

As used herein, the terms "probe" and "biomolecular probe" refer to a biomolecule used to detect a complementary biomolecule. Examples include antigens that detect antibodies, oligonucleotides that detect complimentary oligonucleotides, and ligands that detect receptors. Such probes are preferably immobilized on a microelectrode comprising a substrate.

As used herein, the terms "bioarray," "biochip" and "biochip array" refer to an ordered spatial arrangement of immobilized biomolecules on a microelectrode arrayed on a solid supporting substrate. Preferred probe molecules include aptamers, nucleic acids, oligonucleotides, peptides, ligands, antibodies and antigens; peptides and proteins are the most preferred probe species. Biochips, as used in the art, encompass substrates containing arrays or microarrays, preferably ordered arrays and most preferably ordered, addressable arrays, of biological molecules that comprise one member of a biological binding pair. Typically, such arrays are oligonucleotide arrays comprising a nucleotide sequence that is complementary to at least one sequence that may be or is expected to be present in a biological sample. Alternatively, and preferably, proteins, peptides or other small molecules can be arrayed in such biochips for performing, inter alia, immunological analyses (wherein the arrayed molecules are antigens) or assaying biological receptors (wherein the arrayed molecules are ligands, agonists or antagonists of said receptors).

Expression/amount of a gene, biomolecule, or biomarker in a first sample is at a level "greater than" the level in a second sample if the expression level/amount of the gene or biomarker in the first sample is at least about 1 time, 1.2 times, 1.5 times, 1.75 times, 2 times, 3 times, 4 times, 5 times, 6 times, 7 times, 8 times, 9 times, 10 times, 20 times, 30 times, the expression level/amount of the gene or biomarker in the second sample or a normal sample. Expression levels/amounts can be determined based on any suitable criterion known in the art, including but not limited to mRNA, cDNA, proteins, protein fragments and/or gene copy. Expression levels/amounts can be determined qualitatively and/or quantitatively.

By the term "modulate." it is meant that any of the mentioned activities, are, e.g., increased, enhanced, increased, agonized (acts as an agonist), promoted, decreased, reduced, suppressed blocked, or antagonized (acts as an agonist). Modulation can increase activity more than 1-fold, 2-fold, 3-fold, 5-fold, 10-fold, 100-fold, etc., over baseline values. Modulation can also decrease its activity below baseline values.

An "allele" or "variant" is an alternative form of a gene. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The term, "complementary" means that two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. Normally, the complementary sequence of the oligonucleotide has at least 80% or 90%, preferably 95%, most preferably 100%, complementarity to a defined sequence. Preferably, alleles or variants thereof can be identified. A BLAST program also can be employed to assess such sequence identity.

The term "complementary sequence" as it refers to a polynucleotide sequence, relates to the base sequence in another nucleic acid molecule by the base-pairing rules. More particularly, the term or like term refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 95% of the nucleotides of the other strand, usually at least about 98%, and more preferably from about 99% to about 100%. Complementary polynucleotide sequences can be identified by a variety of approaches including use of well-known computer algorithms and software, for example the BLAST program.

As used herein, the term "aptamer" or "selected nucleic acid binding species" shall include non-modified or chemically modified RNA or DNA. The method of selection may be by, but is not limited to, affinity chromatography and the method of amplification by reverse transcription (RT) or polymerase chain reaction (PCR).

As used herein, the term "signaling aptamer" shall include aptamers with reporter molecules, preferably a fluorescent dye, appended to a nucleotide in such a way that upon conformational changes resulting from the aptamer's interaction with a ligand, the reporter molecules yields a differential signal, preferably a change in fluorescence intensity.

As used herein, the term "fragment or segment", as applied to a nucleic acid sequence, gene or polypeptide, will ordinarily be at least about 5 contiguous nucleic acid bases (for nucleic acid sequence or gene) or amino acids (for polypeptides), typically at least about 10 contiguous nucleic acid bases or amino acids, more typically at least about 20 contiguous nucleic acid bases or amino acids, usually at least about 30 contiguous nucleic acid bases or amino acids, preferably at least about 40 contiguous nucleic acid bases or amino acids, more preferably at least about 50 contiguous nucleic acid bases or amino acids, and even more preferably at least about 60 to 80 or more contiguous nucleic acid bases or amino acids in length. "Overlapping fragments" as used herein, refer to contiguous nucleic acid or peptide fragments which begin at the amino terminal end of a nucleic acid or protein and end at the carboxy terminal end of the nucleic acid or protein. Each nucleic acid or peptide fragment has at least about one contiguous nucleic acid or amino acid position in common with the next nucleic acid or peptide fragment, more preferably at least about three contiguous nucleic acid bases or amino acid positions in common, most preferably at least about ten contiguous nucleic acid bases amino acid positions in common.

"Biological samples" include solid and body fluid samples. Preferably, the sample is obtained from heart. However, the biological samples used in the present invention can include cells, protein or membrane extracts of cells, blood or biological fluids such as ascites fluid or brain fluid (e.g., cerebrospinal fluid). Examples of solid biological samples include, but are not limited to, samples taken from tissues of the central nervous system, bone, breast, kidney, cervix, endometrium, head/neck, gallbladder, parotid gland, prostate, pituitary gland, muscle, esophagus, stomach, small intestine, colon, liver, spleen, pancreas, thyroid, heart, lung, bladder, adipose, lymph node, uterus, ovary, adrenal gland, testes, tonsils and thymus. Examples of "body fluid samples" include, but are not limited to blood, serum, semen, prostate fluid, seminal fluid, urine, saliva, sputum, mucus, bone marrow, lymph, and tears.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair, and the like.

"Diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

Transcriptomic Biomarker/Molecular Signatures

The invention comprises molecular signatures that function as very sensitive diagnostic biomarkers for heart failure, heart diseases, myocarditis, and other heart disorders. These biomarkers also identify individuals at risk of developing cardiovascular diseases or disorders. Myocarditis is a common disease that is estimated to cause up to 30% of dilated cardiomyopathy, even in patients initially asymptomatic. Myocarditis can also present as sudden cardiac death and affects individuals of all ages. In childhood, myocarditis causes a greater percentage of heart failure than in adulthood. The fact that the majority of viral induced cases pass in a clinically unapparent course, points out the significance of finding more reliable biomarkers than standard diagnostic tools which are currently available, e.g. ECG, cardiac enzymes and immunohistochemistry.

Transcriptomics have emerged as a highly valuable tool to aid in complex pathologic diagnosis. A transcriptome was used to create biomarkers (TBBs) that add diagnostic accuracy to clinical, pathological and imaging modalities currently used to diagnose myocarditis.

Derails of the experimental procedures are provided in the examples section which follows. Briefly, a microarray analysis was performed in a case-control fashion on samples from patients with histologically proven myocarditis (n=16) and idiopathic dilated cardiomyopathy (IDCM, n=32) to develop highly accurate diagnostic transcriptomic biomarkers using multiple classification algorithms. Additional gene signatures were obtained to distinguish between cardiac sarcoidosis (n=9), giant cell myocarditis (n=3), peripartum cardiomyopathy (n=6), and systemic lupus erythematosus with cardiac involvement (n=3).

9,878 genes were identified and which were differentially expressed in lymphocytic myocarditis vs. IDCM (FC>1.2, FDR<5%), from which a transcriptomic biomarker containing 62 genes was identified, which distinguished myocarditis with 100% sensitivity (95% CI: 46-100%) and 100% specificity (95% CI: 66-100%). Multiple classification algorithms and quantitative realtime RT-PCR analysis further reduced this subset to a highly robust molecular signature of 13 genes, which still performed with 100% accuracy. TBBs were also obtained to distinguish between giant cell myocarditis and cardiac sarcoidosis, and peripartum cardiomyopathy vs lymphocytic cardiomyopathy.

Transcriptomic biomarkers can improve the clinical detection of patients with inflammatory diseases of the heart. This approach advances the clinical management and treatment of cardiac disorders with highly variable outcome.

In preferred embodiments, diagnosis to distinguish between giant cell myocarditis and cardiac sarcoidosis; peripartum cardiomyopathy vs lymphocytic cardiomyopathy; myocarditis and idiopathic dilated cardiomyopathy; cardiac sarcoidosis, giant cell myocarditis, peripartum cardiomyopathy, and systemic lupus erythematosus with cardiac involvement, comprises identifying a marker signature set forth in any one of Tables 1 to 19, complementary sequences, fragments, alleles, variants and gene products thereof.

For example, a transcriptomic biomarker comprises a molecular signature such as for example: marker signature I: (1552302_at) FLJ77644.TMEM106, (1552553_a_at) NLRC4, (1552584_at) IL12RB1, (1554899_sat) FCER1G, (1555349_a_at) ITGB2, (1559584_a_at) C16orf54, hCG_1644884, (1563245_at) MGST1, (1565162_s_at) ANXA2, (1568126_at) SPP1, (1568574_x_at) IFI30, (201442_at) CTSC, (201487_at) LAPTM5, (201721_s_at) CD14, (201743_at) CAPG, (201850_at) PLTP, (202075_s_at) VAMP8, (202546_at) LYN, (202625_at) ITGB2, (202803_s_at) PCK2, (202847_at) CSF1R, (203104_at) RASSF2, (203185_at) RPS6KA1, (203379_at) CD53, (203416_at) PLEK, (203471_s_at) SEMA4D, (203528_at) CD163, (203645_s_at) PLA2G2A, (203649_s_at) CXCL9, (203915_at) CYBB, (203923_s_at) IRF8, (204057_at) CD48, (204118_at) TYROBP, (204122_at) GLIPR1, (204222_s_at) FCER1G, (204232_at) PLEKHO2, (204436_at) CD44, (204490_s_at) SLC7A7, (204588_s_at) STC 1, (204595_s_at) CD52, (204661_at) VSIG4, (204787_at) IL10RA, (204912_at) SASH3, (204923_at) TLR2, (204924_at) CSTA, (204971_at) CCR1, (205098_at, 205269_at) LCP2, (205270_s_at) GZMA, (205488_at) CD86, (205685_at) CD8A, (205758_at) ITGAM, (205786_s_at) LY86, (205859_at) PTPN6, (206687_s_at) CCR2, FLJ78302, (206978_at) PTPRC, (207238_s_at) SYK, (207540_s_at) LILRB2, (207697_x_at) LCP1, (208885_at) CORO1A, (209083_at) HLA-DQB1, (209480_at) DLK1, (209560_s_at) CD44, (209835_x_at) SPP1, (209875_s_at) A1F1, (209901_x_at) C3AR 1, (209906_at) CD300A, (209933_s_at) NCF2, (209949_at) LILRB2, (210146_x_at) TLR1, (210176_at) LAIR1, (210644_s_at) LILRB1, (211336_x_at) TRBC1, TRBC2, TRBV19; (211796_s_at) CD44, (212063_at) PTPRC, (212587_s_at, 212588_at) HLA-DQA1 HLA-DQA2; (212671_s_at) hCG_1998957. HLA-DQB1/B2, HLA-DRB1/2/3/4/5; (21299_x_at) AIF1, (213095_x_at) DOCK2, (213160_at) HSPA6, (213418_at) RNASE6, (213566_at) RAC2, (213603_s_at) MYO1F, (213733_at) HLA-DQA1, (213831_at) LYZ, (213975_s_at) LOC648998, (214084_x_at) CD163, (215049_x_at) AIF1, (215051_x_at) ADA, (216705_s_at) FCGR1A, FCGR1C; (216950_s_at) GLUL, (217202_s_at) SNX10, (218404_at) MAFB, (218559_s_at) CCDC109B, (218802_at) BIN2, (219191_s_at) DOCK10, (219279_at) SLAMF8, (219386_s_at) SIGLEC1, (219519_s_at) 1-Mar, (219574_at) MS4A4A, (219607_s_at) MS4A6A, (219666_at) GAL3ST4, (219815_at) PSTPIP2, (219938_s_at) TLR7, (220146_at) COTL1, (221059 s_at) NPL, (221210_s_at) SH3BGRL3, (221269_s_at) PYCARD, (221666_s_at) CLEC7A, (221698_s_at) OBFC2A, (222872_x_at) CENTA2, (222876_s_at, 223343_at) MS4A7, (223344_s_at, 223343_at) MS4A6A, (224356_x_at) MS4A4A, (224357_s_at) COTL1, (224583_at) BCAT1, (225285_at) C1QC, (225353_s_at) CTSC, (225646_at) CTSC, (225647_s_at) BCAT1, (226517_at, 226818_at) MPEG1, (226841_at) FYB, (227266_s_at) RILPL2, (227983_at) OSR1, (228399_at) C1orf162, (228532_at) LILRB1, (230741_at) MRO, (231358_at) CTSS, (232617_at) DOCK8, (232843_s_at) OBFC2A, (233085_s_at) PARVG, (234987_at) CPM, (235019_at) HAVCR2, (235458_at) CCL 18, (32128_at) CD52, (34210_at) MAFF, (36711_at) SIGLEC1; or marker signature: (1552411_at) DEFB106A/B, (1556721_at) FLJ33706, (1559224_at) LCE1E, (1562256_at, 1562257_x_at) NLRP1, (1562785_at) HERC6, (1564281_at) LOC285708, (1564362_x_at) ZNF843, (1569568_at) NA, (1569569_x_at) NA, (213609_s_at) SEZ6L, (213791_at) PENK, (224209_s_at) GDA, (231628_s_at) NA, (243909_x_at) GUSBL2, (244891_x_at) NA; or, marker signature II: (1552411_at) DEFB106A/B, (1556721_at) FLJ33706, (1559224_at) LCE1E, (1562256_at, 1562257_x_at) NLRP1, (1562785_at) HERC6, (1564281_at) LOC285708, (1564362_x_at) ZNF843, (1569568_at) NA, (1569569_x_at) NA, (213609_s_at) SEZ6L, (213791_at) PENK, (224209_s_at) GDA, (231628_s_at) NA, (243909_x_at) GUSBL2, (244891_x_at) NA; or, marker signature III: Maf1, MafF, MHC class II, CD44, BCAT1 (*Homo sapiens*); CCR2, BCAT1, ADA, Annexin II, Pleckstrin (*Homo sapiens*); p47-phox, CCR2, p67-phox, Pleckstrin, IL-12 receptor (*Homo sapiens*); C1 q, CD44, CD14, SLAP-130(ADAP), alpha-4/beta-1 integrin (*Homo sapiens*); Plastin, IRT-1 (*Homo sapiens*); CD163, HPIHB complex (*Homo sapiens*); Complement component C1. Complement C4=Complement component C4a$^+$, Complement component C4b, Complement C2=Complement component C2a$^+$, Complement component C2b, PLTP, ABCA 1, CREB1, Cholesterol extracellular region, Cholesterol+ATP+H$_2$O=Cholesterol+ADP+PO$_4$$^{3-}$ (*Homo sapiens*); or, marker signature IV: (156328_at) NA, (204477_at) RABIF, (205275_at) GTPBP1, (214313_s_at) EIF5B; or, marker signature V: (1552302_at) FLJ77644, TMEM106A: (1552310_at) C15orf40, (1553212_at) KRT78, (1555349_a_at) ITGB2, (1555878_at) RPS24, (1556033_at) NA, (1556507_at) NA, (1558605_at) NA (1559224_at) LCE1E, (1562785_at) HERC6, (1565662_at) NA, (1565830_at) NA, (202375_at) SEC24D, (202445_s_at) NOTCH2, (203741_s_at) ADCY7, (204222_s_at) GLIPR1, (206052_s_at) SLBP, (206333_at) MSI1, (206770_s_at) SLC35A3, (209307_at) SWAP70, (211089_s_at) NEK3, (211341_at) LOC100131317, POU4F1; (212511_at) PICALM, (212830_at) MEGF9, (212999_x_at) hCG_1998957. HLA-DQB1/2, HLA-DRB1/2/3/4/5; (213501_at) ACOX1, (213831_at) HLA-DQA1, (217054_at) NA, (217182_at) MUC5AC, (217322_x_at) NA, (217777_s_at) PTPLAD1, (218803_at) CHFR, (219425_at) SULT4A1, (221663_x_at) HRH3, (223077_at) TMOD3, (224327_s_at) DGAT2, (224996_at) Na, (225579_at) PQLC3, (226240_at) MGC21874, (227280_s_at) CCNYL1, (227618_at) Na, (227983_at) RILPL2, (228980_at) RFFL, (229191_at) TBCD, (230836_at) ST8SIA4, (231599_x_at) DPF1, (234495_at) KLK15, (234986_at) NA, (234987_at) NA, (236232_at) STX4, (236404_at) NA, (236698_at) NA, (238327_at) LOC440836, (238445_x_at) MGAT5B, (239463_at) NA, (242383_at) NA, (242563_at) NA, (243819_at) NA, (244841_at) SEC24A, (32069_at) N4BP1, (44673_at) SIGLEC1, (53720_at) C19orf66; or, marker signature VI: MSI1 (1556507_at), KRT78, KRT78 (1556507_at), KRT78 (1556507_at), 1556507_at. Detection of any one or more signatures, combinations of signatures, complementary sequences, fragments, alleles, variants, or gene products thereof, comprise a transcriptomic biomarker.

In another preferred embodiment, a transcriptomic biomarker for the diagnosis between giant cell myocarditis and idiopathic dilated cardiomyopathy comprising a marker signature set forth as: (210667_at) AQP4, (221212_x_at) PBRM1, (227145_at) LOXL4, (228329_at) DAB1, (231577_s_at) GBP1, (231906_at) HOXD8, (235334_at) ST6GALNAC3, (237783_at) PLAC8L1, complementary sequences, fragments, alleles, variants and gene products thereof.

In another preferred embodiment, a transcriptomic biomarker for the diagnosis between sarcoidosis and idiopathic dilated cardiomyopathy comprising a marker signature set forth as: (1552974_at) NA, (1553781_at) ZC3HAV1L, (1554478_a_at) HEATR3, (1556760_a_at) NA, (1556883_a_at) LOC440896, (1557717_at) LOC338862, (1560144-at) NA, (1560683_at) BCL8, (1560684_x_at) BCL8, (1561543_at) NA, (1562035_at) NA, (1563054_at) NA, (1563452_at) KIAA0241, (1564107_at) NA, (1564733_at) NA, (1565788_at) NA, (1566550_at) NA, (1568589_at) NA, (201291_s_at) TOP2A, (204666_s_at) RP5-1000E10.4, (208356_s_at) BCL2L11, (209371_s_at) SH3BP2, (215512_at) 6-Mar, (216947_at) DES, (217292_at) MTMR7, (218554_s_at) ASH1L, (218585_s_at) DTL, (219528_at) TIPIN (219735_sat) TFCP2L1, (219918_s_at) ASPM, (220085_at) HELLS, (220735_s_at) SENP7, (220930_s_at) MGC5590, (221212_x_at) PBRM1, (221268_s_at) SGPP1, (221969_at) NA, (223700_at) MND1, (223865_at) SOX6, (224424_x_at) LOC440888, (224426_s_at) LOC440888, (232453_at) NA, (233786_at) NA, (235588_at) ESCO2, (235661_at) NA, (235899_at) CA13, (236628_at) NA, (236470_at) NA, (237289_at) CREB1, (238370_x_at) RPL22, (238375_at, 239486_at) NA, (239899_at) RNF145, (241922_at) NA, (242784_at) NA, (242939_at) TFDP1, (244356_at) NA, (244609_at) NA, (37892_at) COL11A1, complementary sequences, fragments, alleles, variants and gene products thereof.

In another preferred embodiment, a transcriptomic biomarker for the diagnosis between peripartum cardiomyopathy and idiopathic dilated cardiomyopathy comprising a marker signature set forth as: (1553972_a_at) CBS, (1557833_at) NA, (1560395_at) NA; (201909_at) LOC100133662, RPS4Y1; (204409_s_at, 204410_at) EIF1AY, (205000_at, 205001_s_at) DDX3Y; (205033_s_at) DEFA1, DEFA3, LOC728358; (205048_s_at) PSPH, (205609_at) ANGPT1, (206624_at) LOC100130216, USP9Y; (206700_s_at) JARID1D, (207063_at) CYorf14, (208067_x_at) LOC100130224, UTY; (209771_x_at) CD24, (211018_at) LSS, (211149_at) LOC100130224, UTY; (212768_s_at) OLFM4, (212816_s_at) CBS, (212906_at) GRAMD1B, (214131_at) CYorf15B, (214218_s_at) XIST, (214983_at) TTTY15, (216758_at) NA, (219938_s_at) PSTPIP2, (221728_x_at) XIST, (223645_s_at, 223646_s_at) CYorf15B, (224293_at) TTTY10, (224588_at, 224589_at, 224590_at, 227671_at) XIST, (227742_at) CLIC6, (228194_s_at) SORCS1, (228492_at) LOC100130216, USP9Y; (221960_at) MUM1L1, (229534_at) ACOT4, (230104_s_at) TPPP, (230760_at) LOC100130829, ZFY; (231592_at) TSIX, (232365_at) SIAH1, (232618_at) CYorf15A, (233176_at) NA, (235334_at) ST6GALNAC3, (235446_at) NA, (235942_at) LOC401629, LOC401630, (236694_at) CYorf15A, (239568_at) PLEKHH2, (239584_at) NA, (239677_at) NA, (24316_at) NA, (243610_at) C9orf135, (244482_at) Na, (226_s_at) CD24, complementary sequences, fragments, alleles, variants and gene products thereof.

In another preferred embodiment, a transcriptomic biomarker for the diagnosis between systemic lupus erythematosus and idiopathic dilated cardiomyopathy comprising a marker signature set forth as: (1552946_at) ZNF114, (1553607_at) C21orf109, (1555485_s_at) FAM153B, (1558882_at) LOC401233, (1561012_at) NA, (1566518_at) NA, (1569539_at) NA, (1569794_at) NA, (207781_s_at) ZNF711, (222375_at) NA, (229288_at) NA, (229523_at) TTMA, (235803_at) NA, (238553_at) EPHA7, (238755_at) NA, (240783_at) NA, (240903_at) NA, (242641_at) NA, (243012_at) NA, (244626_at) NA, (244636_at) NA, complementary sequences, fragments, alleles, variants and gene products thereof.

In another preferred embodiment, a transcriptomic biomarker for the diagnosis between giant cell myocarditis and lymphocytic myocarditis comprising the marker signature set forth as: (156328_at) NA, (204477_at) RABIF, (205275_at) GTPBP1, (214313_s_at) EIF5B, complementary sequences, fragments, alleles, variants and gene products thereof.

In another preferred embodiment, a transcriptomic biomarker for the diagnosis between sarcoidosis and lymphocytic myocarditis comprising a marker signature set forth as:

(20447_at) RABIF, (205275_at) GTPBP1, (214313_s_at) EIF5B, (224500_s_at) MON 1A, (236093_at) NA, (243564_at) PDE1C, complementary sequences, fragments, alleles, variants and gene products thereof.

In another preferred embodiment, a transcriptomic biomarker for the diagnosis between peripartum cardiomyopathy and lymphocytic myocarditis comprising a marker signature set forth as: (156328_at) NA, (205275_at) GTPBP1, (207300_s_at) F7, (214313_s_at) EIF5B, (214473_x_at) PMS2L3, (227509_x_at) NA, (228232_s_at) VSIG2, (230731_x_at) ZDHHC8, (232586_x_at) LOC100133315, (236093_at) NA, (237867_s_at) PID1, (243564_at) PDE1C, complementary sequences, fragments, alleles, variants and gene products thereof.

In another preferred embodiment, a transcriptomic biomarker for the diagnosis between systemic lupus erythematosus and lymphocytic myocarditis comprising a marker signature set forth as: (1556205_at) NA, (202179_at) BLMH, (203134_at) PICALM, (203540_at) GFAP, (205554_s_at) DNASE1L3, (205673_s_at) ASB9, (205794_s_at) NOVA1, (209220_at) GPC3, (209304_x_at) GADD45B, (209540_at) IGF1, (209923_s_at) BRAP, (212173_at) AK2, (213469_at) LPPR4 (214338_at) DNAJB12, (216269_s_at) ELN, (217950_at) NOSIP, (218180_s_at) EPS8L2, (220117_at) ZNF385D, (220941_s_at) C21orf91, (222002_at) C7orf26, (222879_s_at) POLH, (223574_x_at) PPP2R2C, (223586_at) ARNTL2, (230974_at) DDX19B, (233298_at) C13orf38, SOHLH2; (238151_at) NA, (243076_x_at) GLI4, complementary sequences, fragments, alleles, variants and gene products thereof.

In another preferred embodiment, a transcriptomic biomarker for the differential diagnosis between giant cell myocarditis and sarcoidosis comprising a marker signature set forth as: (1553894_at) CCDC122, (1557311_at) LOC100131354, (1557996_at) POLR2J4, (1558430_at) NA, (1559227_s_at) VHL, (1561789_at) NA, (1569312_at) NA, (205238_at) CXorf34, (211734_s_at) FCER1A, (218699_at) RAP2C, (225207_at) PDK4, (231114_at) SPATA22, (231418_at) NA, (231819_at) NA, (231956_at) KIAA1618, (233927_at) NA, (239151_at) CTGLF6, (241788_x_at) NA, (242691_at) NA, complementary sequences, fragments, alleles, variants and gene products thereof.

In another preferred embodiment, a transcriptomic biomarker for the diagnosis of myocarditis comprising a marker signature set forth as: (1552302_at) FLJ77644, TMEM106A; (1552310_at) C15orf40, (1553212_at) KRT78, (1555349_a_at) ITGB2, (1555878_at) RPS24, (1556033_at) NA, (1556507_at) NA, (1558605_at) NA (1559224_at) LCE1E, (1562785_at) HERC6, (1565662_at) NA, (1565830_at) NA, (202375_at) SEC24D, (202445_s_at) NOTCH2, (203741_s_at) ADCY7, (204222_s_at) GLIPR1, (206052_s_at) SLBP, (206333_at) MSI1, (206770_s_at) SLC35A3, (209307_at) SWAP70, (211089_s_at) NEK3, (211341_at) LOC100131317, POU4F1; (212511_at) PICALM, (212830_at) MEGF9, (212999_x_at) hCG_1998957, HLA-DQB1/2, HLA-DRB1/2/3/4/5; (213501_at) ACOX1, (213831_at) HLA-DQA1, (217054_at) NA, (217182_at) MUC5AC, (217322_x_at) NA, (217777_s_at) PTPLAD1, (218803_at) CHFR, (219425_at) SULT4A1, (221663_x_at) HRH3, (223077_at) TMOD3, (224327_s_at) DGAT2, (224996_at) Na, (225579_at) PQLC3, (226240_at) MGC21874, (227280_s_at) CCNYL1, (227618_at) Na, (227983_at) RILPL2, (228980_at) RFFL, (229191_at) TBCD, (230836_at) ST8SIA4, (231599_x_at) DPF1, (234495_at) KLK15, (234986_at) NA, (234987_at) NA, (236232_at) STX4, (236404_at) NA, (236698_at) NA, (238327_at) LOC440836, (238445_x_at) MGAT5B, (239463_at) NA, (242383_at) NA, (242563_at) NA, (243819_at) NA, (244841_at) SEC24A, (32069_at) N4BP1, (44673_at) SIGLEC1, (53720_at) C19orf66, complementary sequences, fragments, alleles, variants and gene products thereof.

In another preferred embodiment, a transcriptomic biomarker for the diagnosis of myocarditis versus idiopathic dilated cardiomyopathy comprising a marker signature set forth as: MSI1 (1556507_at), KRT78, KRT78 (1556507_at), KRT78 (1556507_at), 1556507_at, complementary sequences, fragments, alleles, variants and gene products thereof.

In another preferred embodiment, a transcriptomic biomarker for the diagnosis and differential diagnosis between myocarditis and idiopathic dilated cardiomyopathy comprising the marker signatures set forth in Tables 1, 2, 3, or 15, complementary sequences, fragments, alleles, variants and gene products thereof.

In another preferred embodiment, a transcriptomic biomarker for the diagnosis between giant cell myocarditis and idiopathic dilated cardiomyopathy comprising the marker signatures set forth in Table 4, complementary sequences, fragments, alleles, variants and gene products thereof.

In another preferred embodiment, a transcriptomic biomarker for the diagnosis between sarcoidosis and idiopathic dilated cardiomyopathy comprising the marker signature set forth in Table 5, complementary sequences, fragments, alleles, variants and gene products thereof.

In another preferred embodiment, a transcriptomic biomarker for the diagnosis between peripartum cardiomyopathy and idiopathic dilated cardiomyopathy comprising the marker signature set forth in Table 6, complementary sequences, fragments, alleles, variants and gene products thereof.

In another preferred embodiment, a transcriptomic biomarker for the diagnosis between systemic lupus erythematosus and idiopathic dilated cardiomyopathy comprising the marker signature set forth in Table 7, complementary sequences, fragments, alleles, variants and gene products thereof.

In another preferred embodiment, a transcriptomic biomarker for the diagnosis between giant cell myocarditis and lymphocytic myocarditis comprising the marker signature set forth in Table 8, complementary sequences, fragments, alleles, variants and gene products thereof.

In another preferred embodiment, a transcriptomic biomarker for the diagnosis between sarcoidosis and lymphocytic myocarditis comprising the marker signature set forth in Table 9, complementary sequences, fragments, alleles, variants and gene products thereof.

In another preferred embodiment, a transcriptomic biomarker for the diagnosis between peripartum cardiomyopathy and lymphocytic myocarditis comprising the marker signature set forth in Table 10, complementary sequences, fragments, alleles, variants and gene products thereof.

In another preferred embodiment, a transcriptomic biomarker for the diagnosis between systemic lupus erythematosus and lymphocytic myocarditis comprising the marker signature set forth in Table 11, complementary sequences, fragments, alleles, variants and gene products thereof.

In another preferred embodiment, a transcriptomic biomarker for the diagnosis between giant cell myocarditis and sarcoidosis comprising the marker signature set forth in Table 12, complementary sequences, fragments, alleles, variants and gene products thereof.

In another preferred embodiment, a transcriptomic biomarker for the diagnosis of myocarditis comprising the marker signature set forth in Table 14, complementary sequences, fragments, alleles, variants and gene products thereof.

In another preferred embodiment, a transcriptomic biomarker for the diagnosis of subtypes of inflammatory cardiomyopathy vs idiopathic dilated cardiomyopathy comprising the marker signatures set forth in Table 18, complementary sequences, fragments, alleles, variants and gene products thereof.

In another preferred embodiment, a transcriptomic biomarker for the diagnosis of rare types of inflammatory cardiomyopathy vs lymphocytic myocarditis comprising the marker signatures set forth in Table 19, complementary sequences, fragments, alleles, variants and gene products thereof.

In another preferred embodiment, comprises an antibody or aptamer specific for each gene sequence set froth in Tables 1 to 19, complementary sequences, fragments, alleles, variants and gene products thereof, complementary sequences, fragments, alleles, variants and gene products thereof.

In another preferred embodiment, a biochip comprising nucleic acid sequences set forth in Tables 1 to 19, complementary sequences, fragments, alleles, variants and gene products thereof.

A method of diagnosing myocarditis and other cardiac disorders, comprising: identifying in a biological sample from a patient a molecular signature set forth in Tables 1 to 19, complementary sequences, fragments, alleles, variants and gene products thereof; assessing the probability of identification of each component gene in each sample; assigning each to a class; and, diagnosing myocarditis and other cardiac disorders.

In another preferred embodiment, a method of diagnosing heart disease or myocarditis comprising: identifying in a biological sample from a patient a molecular signature set forth in Tables 1 to 19, complementary sequences, fragments, alleles, variants and gene products thereof; assessing the probability of identification of each component gene in each sample; assigning each to a class; and, diagnosing heart disease or myocarditis.

In another preferred embodiment, a kit comprising a transcriptomic biomarker of any one or more molecular signatures set forth in Tables 1 to 19.

In another preferred embodiment, a cell expressing any one or more biomolecules selected from Tables 1 to 19.

In another preferred embodiment, a vector encoding any one or more biomolecules selected from Tables 1 to 19.

In another preferred embodiment, the detection in a cell or patient of the biomolecules, complementary sequences, fragments, alleles, variants and gene products thereof, is diagnostic of myocarditis, idiopathic cardiomyopathy, heart diseases and disorders thereof. Preferably, the biomolecule sequences, complementary sequences, fragments, alleles, variants and gene products thereof, are modulated at levels by at least between 1%, 2%, 5%, 10%/o in a cell or patient as compared to levels in a normal cell or normal subject; more preferably, the gene biomarker sequences, complementary sequences, fragments, alleles, variants and gene products thereof, are modulated by about 50% in a cell or a patient as compared to levels in a normal cell or normal subject; more preferably, the gene biomarker sequences, complementary sequences, fragments, alleles, variants and gene products thereof, are modulated by about 75% in a cell or a patient as compared to levels in a normal cell or normal subject. The term "modulated" refers to an increase or decrease in level, concentration, amount etc, as compared to a normal cell or normal healthy subject. The term can also be applied as "differential expression" wherein one or more markers are increased, decreased or remain at baseline levels relative to each other and baseline normal controls.

Alternative Methods and Materials for Identifying Molecular Signatures or Transcriptomic Biomarkers Detection of Nucleic Acids and Proteins as Markers:

In preferred embodiments, each biomarker is detected on chip based methods such as those described in detail in the examples which follow. In order to provide accurate diagnosis of cardiac disorders and diseases, for example, heart failure, myocarditis, idiopathic cardiomyopathy and the like. Other methods are also known in the art and one or more methods can be utilized.

The methods and assays disclosed herein are directed to the examination of expression of transcriptomic biomarkers in a mammalian tissue or cell sample, wherein the determination of that expression of one or more such transcriptomic biomarkers is predictive of prognostic outcome or diagnostic of cardiac and cardiovascular diseases and disorders, such as for example, myocarditis, Coronary Heart Disease, angina, Acute Coronary Syndrome, Aortic Aneurysm and Dissection, arrhythmias, Cardiomyopathy, Congenital Heart Disease, congestive heart failure or chronic heart failure, pericarditis, and the like. The Molecular signatures or Transcriptomic biomarker comprise the biomolecules identified in Tables 1 to 19.

Preferred embodiments in the identification of biomolecules, analytical methods etc, are described in detail in the Examples which follow.

Microarryas:

In general, using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment. (see, e.g., WO 01/75166 published Oct. 11, 2001; (See, for example, U.S. Pat. Nos. 5,700,637, 5,445,934, and 5,807,522, Lockart, *Nature Biotechnology,* 14:1675-1680 (1996); Cheung, V. G. et al., *Nature Genetics* 21(Suppl):15-19 (1999) for a discussion of array fabrication). DNA microarrays are miniature arrays containing gene fragments that are either synthesized directly onto or spotted onto glass or other substrates. Thousands of genes are usually represented in a single array. A typical microarray experiment involves the following steps: 1) preparation of fluorescently labeled target from RNA isolated from the sample, 2) hybridization of the labeled target to the microarray, 3) washing, staining, and scanning of the array, 4) analysis of the scanned image and 5) generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ). The Affymetrix GENECHIP™ system is a commercially available microarray system which comprises arrays fabricated by direct synthesis of oligonucleotides on a glass surface.

Probe/Gene Arrays:

Oligonucleotides, usually 25 mers, are directly synthesized onto a glass wafer by a combination of semiconductor-based photolithography and solid phase chemical synthesis technologies. Each array contains up to 400,000 different oligonucleotides and each oligonucleotide is present in millions of copies. Since oligonucleotide probes are synthesized in known locations on the array, the hybridization patterns and signal intensities can be interpreted in terms of gene identity and relative expression levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligonucleotide. The Microarray Suite software subtracts the hybridization intensities of the mismatch probes from those of the perfect match probes to determine the absolute or specific intensity value for each probe set. Probes are chosen based on current information from GenBank and other nucleotide repositories. The sequences are believed to recognize unique regions of the 3' end of the gene. A GeneChip Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

The expression of a selected biomarker may also be assessed by examining gene deletion or gene amplification. Gene deletion or amplification may be measured by any one of a wide variety of protocols known in the art, for example, by conventional Southern blotting. Northern blotting to quantitate the transcription of mRNA (Thomas, *Proc. Natl. Acad. Sci. USA*, 77:5201-5205 (1980)), dot blotting (DNA analysis), or in situ hybridization (e.g., FISH), using an appropriately labeled probe, cytogenetic methods or comparative genomic hybridization (CGH) using an appropriately labeled probe.

Detection of Polypeptides:

In another embodiment of the present invention, a polypeptide corresponding to a marker is detected. A preferred agent for detecting a polypeptide of the invention is an antibody or aptamer capable of binding to a polypeptide corresponding to a marker of the invention, preferably an antibody with a detectable label. Antibodies can be polyclonal, or more preferably, monoclonal. An intact antibody, or a fragment thereof, e.g., Fab or $F(ab')_2$ can be used. The term "labeled", with regard to the probe or antibody, is intended to encompass direct-labeling of the probe or antibody by coupling, i.e., physically linking, a detectable substance to the probe or antibody, as well as indirect-labeling of the probe or antibody by reactivity with another reagent that is directly-labeled. Examples of indirect labeling include detection of a primary antibody using a fluorescently-labeled secondary antibody and end-labeling of a DNA probe with biotin such that it can be detected with fluorescently-labeled streptavidin.

Proteins from individuals can be isolated using techniques that are well-known to those of skill in the art. The protein isolation methods employed can, e.g., be such as those described in Harlow & Lane (1988), supra. A variety of formats can be employed to determine whether a sample contains a protein that binds to a given antibody. Expression of various biomarkers in a sample can be analyzed by a number of methodologies, many of which are known in the art and understood by the skilled artisan, including but not limited to, immunohistochemical and/or Western analysis, quantitative blood based assays (as for example Serum ELISA) (to examine, for example, levels of protein expression), biochemical enzymatic activity assays, in situ hybridization, Northern analysis and/or PCR analysis of mRNAs, as well as any one of the wide variety of assays that can be performed by gene and/or tissue array analysis. Typical protocols for evaluating the status of genes and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). A skilled artisan can readily adapt known protein/antibody detection methods for use in determining whether cells express a marker of the present invention and the relative concentration of that specific polypeptide expression product in blood or other body tissues.

In such alternative methods, a sample may be contacted with an antibody specific for said biomarker under conditions sufficient for an antibody-biomarker complex to form, and then detecting said complex. The presence of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful and commonly used assays. A number of variations of the sandwich assay technique exist, and all are intended to be encompassed by the present invention. Briefly, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

An alternative method involves immobilizing the target biomarkers in the sample and then exposing the immobilized target to specific antibody which may or may not be labeled with a reporter molecule. Depending on the amount of target and the strength of the reporter molecule signal, a bound target may be detectable by direct labeling with the antibody. Alternatively, a second labeled antibody, specific to the first antibody is exposed to the target-first antibody complex to form a target-first antibody-second antibody tertiary complex. The complex is detected by the signal emitted by the reporter molecule. By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, -galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample. Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art. However, other reporter molecules, such as radioisotope, chemiluminescent or bioluminescent molecules, may also be employed.

Methods of the invention further include protocols which examine the presence and/or expression of mRNAs, in a tissue or cell sample. Methods for the evaluation of mRNAs in cells are well known and include, for example, hybridization assays using complementary DNA probes (such as in situ hybridization using labeled riboprobes, Northern blot and related techniques) and various nucleic acid amplification assays (such as RT-PCR and other amplification type detection methods, such as, for example, branched DNA, SISBA, TMA and the like).

In an embodiment, the level of mRNA corresponding to the marker can be determined both by in situ and by in vitro formats in a biological sample using methods known in the art. Many expression detection methods use isolated RNA. For in vitro methods, any RNA isolation technique that does not select against the isolation of mRNA can be utilized for the purification of RNA from cells. See, e.g., Ausubel et al., Ed., Curr. Prot. Mol. Biol., John Wiley & Sons, NY (1987-1999). Additionally, large numbers of tissue samples can readily be processed using techniques well-known to those of skill in the art, such as, e.g., the single-step RNA isolation process of U.S. Pat. No. 4,843,155. The isolated mRNA can be used in hybridization or amplification assays that include, but are not limited to, Southern or Northern analyses, PCR analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, e.g., a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example, by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

Although amplification of molecules is not required in the present invention as discussed in the examples section, one of skill in the art could use amplification methods. One alternative method for determining the level of mRNA corresponding to a marker of the present invention in a sample involves the process of nucleic acid amplification, e.g., by RT-PCR (the experimental embodiment set forth in Mullis, U.S. Pat. No. 4,683,202 (1987); ligase chain reaction, self-sustained sequence replication, Guatelli et al., Proc. Natl. Acad Sci. USA, Vol. 87, pp. 1874-1878 (1990); transcriptional amplification system, Kwoh et al., Proc. Natl. Acad. Sci. USA, Vol. 86, pp. 1173-1177 (1989); Q-Beta Replicase, Lizardi et al., Biol. Technology, Vol. 6, p. 1197 (1988); rolling circle replication, U.S. Pat. No. 5,854,033 (1988); or any other nucleic acid amplification method, followed by the detection of the amplified molecules using techniques well-known to those of skill in the art. These detection schemes are especially useful for the detection of the nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10-30 nucleotides in length and flank a region from about 50-200 nucleotides in length. Under appropriate conditions and with appropriate reagents, such primers permit the amplification of a nucleic acid molecule comprising the nucleotide sequence flanked by the primers.

For in situ methods, mRNA does not need to be isolated form the cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes, such as the actin gene or epithelial cell-specific genes. This normalization allows the comparison of the expression level in one sample, e.g., a patient sample, to another sample or between samples from different sources.

Alternatively, the expression level can be provided as a relative expression level. To determine a relative expression level of a marker, the level of expression of the marker is determined for 10 or more samples of normal versus disease biological samples, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

Preferably, the samples used in the baseline determination will be from patients who do not have the polymorphism. The choice of the cell source is dependent on the use of the relative expression level. Using expression found in normal tissues as a mean expression score aids in validating whether the marker assayed is specific (versus normal cells). In addition, as more data is accumulated, the mean expression value can be revised, providing improved relative expression values based on accumulated data.

Antibodies and Aptamers

In a preferred embodiment, the antibodies and aptamers specifically bind each component of the biomarkers described herein. The components include the nucleic acid sequences, complementary sequences, fragments, alleles, variants and gene products thereof of each component in each biomarker.

Aptamer polynucleotides are typically single-stranded standard phosphodiester DNA (ssDNA). Close DNA analogs can also be incorporated into the aptamer as described below.

A typical aptamer discovery procedure is described below: A polynucleotide comprising a randomized sequence between "arms" having constant sequence is synthesized. The arms can include restriction sites for convenient cloning and can also function as priming sites for PCR primers. The synthesis can easily be performed on commercial instruments.

The target protein is treated with the randomized polynucleotide. The target protein can be in solution and then the complexes immobilized and separated from unbound nucleic acids by use of an antibody affinity column. Alternatively, the target protein might be immobilized before treatment with the randomized polynucleotide.

The target protein-polynucleotide complexes are separated from the uncomplexed material and then the bound polynucleotides are separated from the target protein. The bound nucleic acid can then be characterized, but is more commonly amplified, e.g. by PCR and the binding, separation and amplification steps are repeated. In many instances, use of conditions increasingly promoting separation of the nucleic acid from the target protein, e.g. higher salt concentration, in the binding buffer used in step 2) in subsequent iterations, results in identification of polynucleotides having increasingly high affinity for the target protein.

The nucleic acids showing high affinity for the target proteins are isolated and characterized. This is typically accomplished by cloning the nucleic acids using restriction sites incorporated into the arms, and then sequencing the cloned nucleic acid.

The affinity of aptamers for their target proteins is typically in the nanomolar range, but can be as low as the picomolar range. That is $K_D$ is typically 1 pM to 500 nM, more typically from 1 pM to 100 nM. Aptamers having an affinity of $K_D$ in the range of 1 pM to 10 nM are also useful.

Aptamer polynucleotides can be synthesized on a commercially available nucleic acid synthesizer by methods known in the art. The product can be purified by size selection or chromatographic methods.

Aptamer polynucleotides are typically from about 10 to 200 nucleotides long, more typically from about 10 to 100 nucleotides long, still more typically from about 10 to 50 nucleotides long and yet more typically from about 10 to 25 nucleotides long. A preferred range of length is from about 10 to 50 nucleotides.

The aptamer sequences can be chosen as a desired sequence, or random or partially random populations of sequences can be made and then selected for specific binding to a desired target protein by assay in vitro. Any of the typical nucleic acid-protein binding assays known in the art can be used, e.g. "Southwestern" blotting using either labeled oligonucleotide or labeled protein as the probe. See also U.S. Pat. No. 5,445,935 for a fluorescence polarization assay of protein-nucleic acid interaction.

Appropriate nucleotides for aptamer synthesis and their use, and reagents for covalent linkage of proteins to nucleic acids and their use, are considered known in the art. A desired aptamer-protein complex, for example, aptamer-thrombin complex of the invention can be labeled and used as a diagnostic agent in vitro in much the same manner as any specific protein-binding agent, e.g. a monoclonal antibody. Thus, an aptamer-protein complex of the invention can be used to detect and quantitate the amount of its target protein in a sample, e.g. a blood sample, to provide diagnosis of a disease state correlated with the amount of the protein in the sample.

A desired aptamer-target/bait molecular complex can also be used for diagnostic imaging. In imaging uses, the complexes are labeled so that they can be detected outside the body. Typical labels are radioisotopes, usually ones with short half-lives. The usual imaging radioisotopes, such as $^{123}$I, $^{124}$I, $^{125}$I, $^{131}$I, $^{99m}$TC, $^{186}$Re, $^{188}$Re, $^{64}$Cu, $^{67}$Cu, $^{212}$Bi, $^{213}$Bi, $^{67}$Ga, $^{90}$Y, $^{111}$In, $^{18}$F, $^{3}$H, $^{14}$C, $^{31}$S or $^{32}$P can be used. Nuclear magnetic resonance (NMR) imaging enhancers, such as gadolinium-153, can also be used to label the complex for detection by NMR. Methods and reagents for performing the labeling, either in the polynucleotide or in the protein moiety, are considered known in the art.

In a preferred embodiment, an antibody or aptamer is specific for each biomolecule of in Tables 1 to 19.

Drug Discovery

In other preferred embodiments, the molecular signatures are useful for the identification of new drugs in the treatment of cardiovascular diseases and disorders.

In another preferred embodiment, the molecular signatures would verify whether a patient's treatment is progressing. For example, the molecular signature may change during the course of treatment and reflect normal controls.

Small Molecules:

Small molecule test compounds or candidate therapeutic compounds can initially be members of an organic or inorganic chemical library. As used herein, "small molecules" refers to small organic or inorganic molecules of molecular weight below about 3,000 Daltons. The small molecules can be natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, *Curr. Opin. Chem. Bio.*, 1:60 (1997). In addition, a number of small molecule libraries are commercially available.

Particular screening applications of this invention relate to the testing of pharmaceutical compounds in drug research. The reader is referred generally to the standard textbook "In vitro Methods in Pharmaceutical Research", Academic Press, 1997, and U.S. Pat. No. 5,030,015). Assessment of the activity of candidate pharmaceutical compounds generally involves administering a candidate compound, determining any change in the morphology, marker phenotype and expression, or metabolic activity of the cells and function of the cells that is attributable to the compound (compared with untreated cells or cells treated with an inert compound), and then correlating the effect of the compound with the observed change.

The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug-drug interaction effects. In some applications, compounds are screened initially for potential toxicity (Castell et al., pp. 375-410 in "In vitro Methods in Pharmaceutical Research," Academic Press, 1997). Cytotoxicity can be determined in the first instance by the effect on cell viability, survival, morphology, and expression or release of certain markers, receptors or enzymes. Effects of a drug on chromosomal DNA can be determined by measuring DNA synthesis or repair. [$^{3}$H] thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (PP 375-410 in "In vitro Methods in Pharmaceutical Research," Academic Press, 1997) for further elaboration.

In one embodiment of the invention, a method of identifying a candidate agent is provided said method comprising: (a) contacting a biological sample from a patient with the candidate agent and determining the level of expression of one or more biomarkers described herein; (b) determining the level of expression of a corresponding biomarker or biomarkers in an aliquot of the biological sample not contacted with the candidate agent; (c) observing the effect of the candidate agent by comparing the level of expression of the biomarker or biomarkers in the aliquot of the biological sample contacted with the candidate agent and the level of expression of the corresponding biomarker or biomarkers in the aliquot of the biological sample not contacted with the candidate agent; and (d) identifying said agent from said observed effect, wherein an at least 1%, 2%, 5%, 10% difference between the level of expression of the biomarker gene or combination of biomarker genes in the aliquot of the biological sample contacted with the candidate agent and the level of expression of the corresponding biomarker gene or combination of biomarker genes in the aliquot of the biological sample not contacted with the candidate agent is an indication of an effect of the candidate agent.

In preferred embodiments, the effects of the drug are correlated with the expression of the molecular signatures associated with a good prognosis as described in detail in the examples which follow.

In another embodiment of the invention, a candidate agent derived by the method according to the invention is provided.

In another embodiment of the invention, a pharmaceutical preparation comprising an agent according to the invention is provided.

In another preferred embodiment of the invention, a method of producing a drug comprising the steps of the method according to the invention (i) synthesizing the candidate agent identified in step (c) above or an analog or derivative thereof in an amount sufficient to provide said drug in a therapeutically effective amount to a subject; and/or (ii) combining the drug candidate the candidate agent identified in step (c) above or an analog or derivative thereof with a pharmaceutically acceptable carrier.

Vectors, Cells:

In some embodiments it is desirable to express the biomolecules that comprise a biomarker, in a vector and in cells. The applications of such combinations are unlimited. The vectors and cells expressing the one or more biomolecules can be used in assays, kits, drug discovery, diagnostics, prognostics and the like. The cells can be stem cells isolated from the bone marrow as a progenitor cell, or cells obtained from any other source, such as for example, ATCC.

"Bone marrow derived progenitor cell" (BMDC) or "bone marrow derived stem cell" refers to a primitive stem cell with the machinery for self-renewal constitutively active. Included in this definition are stem cells that are totipotent, pluripotent and precursors. A "precursor cell" can be any cell in a cell differentiation pathway that is capable of differentiating into a more mature cell. As such, the term "precursor cell population" refers to a group of cells capable of developing into a more mature cell. A precursor cell population can comprise cells that are totipotent, cells that are pluripotent and cells that are stem cell lineage restricted (i.e. cells capable of developing into less than all hematopoietic lineages, or into, for example, only cells of erythroid lineage). As used herein, the term "totipotent cell" refers to a cell capable of developing into all lineages of cells. Similarly, the term "totipotent population of cells" refers to a composition of cells capable of developing into all lineages of cells. Also as used herein, the term "pluripotent cell" refers to a cell capable of developing into a variety (albeit not all) lineages and are at least able to develop into all hematopoietic lineages (e.g., lymphoid, erythroid, and thrombocytic lineages). Bone marrow derived stem cells contain two well-characterized types of stem cells. Mesenchymal stem cells (MSC) normally form chondrocytes and osteoblasts. Hematopoietic stem cells (HSC) are of mesodermal origin that normally gives rise to cells of the blood and immune system (e.g., erythroid, granulocyte/macrophage, magakaryocite and lymphoid lineages). In addition, hematopoietic stem cells also have been shown to have the potential to differentiate into the cells of the liver (including hepatocytes, bile duct cells), lung, kidney (e.g., renal tubular epithelial cells and renal parenchyma), gastrointestinal tract, skeletal muscle fibers, astrocytes of the CNS, Purkinje neurons, cardiac muscle (e.g., cardiomyocytes), endothelium and skin.

In a preferred embodiment, a method of identifying candidate therapeutic compounds comprises culturing cells expressing at least one biomolecule selected from biomarker signatures in Tables 1 to 19.

Such compounds are useful, e.g., as candidate therapeutic compounds for the treatment of heart disease, heart disorders and conditions thereof. Thus, included herein are methods for screening for candidate therapeutic compounds for the treatment of, for example, myocarditis, Coronary Heart Disease, angina, Acute Coronary Syndrome, Aortic Aneurysm and Dissection, arrhythmias, Cardiomyopathy. Congenital Heart Disease, congestive heart failure or chronic heart failure, pericarditis, and the like. The methods include administering the compound to a model of the condition, e.g., contacting a cell (in vitro) model with the compound, or administering the compound to an animal model of the condition, e.g., an animal model of a condition associated with heart disease. The model is then evaluated for an effect of the candidate compound on the clinical outcome in the model and can be considered a candidate therapeutic compound for the treatment of the condition. Such effects can include clinically relevant effects, decreased pain; increased life span; and so on. Such effects can be determined on a macroscopic or microscopic scale. Candidate therapeutic compounds identified by these methods can be further verified, e.g., by administration to human subjects in a clinical trial.

The biomolecules can be expressed from one or more vectors. A "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy. Vectors include, for example, viral vectors (such as adenoviruses ("Ad"), adeno-associated viruses (AAV), and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; *BioTechniques*. 34: 167-171 (2003). Large varieties of such vectors are known in the art and are generally available.

In another preferred embodiment, a vector expresses one or more biomolecules identified in any one or more of Tables 1 to 19.

Kits

In another preferred embodiment, a kit is provided comprising any one or more of the biomarkers or molecular signatures comprising Tables 1 to 19.

For use in the applications described or suggested above, kits or articles of manufacture are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

The kits of the invention have a number of embodiments. A typical embodiment is a kit comprising a container, a label on said container, and a composition contained within said container; wherein the composition includes a primary antibody that binds to the biomolecules of each molecular signature and instructions for using the antibody for evaluating the presence of biomolecules in at least one type of mammalian cell. The kit can further comprise a set of instructions and materials for preparing a tissue sample and applying antibody and probe to the same section of a tissue sample. The kit may include both a primary and secondary antibody, wherein the secondary antibody is conjugated to a label, e.g., an enzymatic label.

Another embodiment is a kit comprising a container, a label on said container, and a composition contained within said container; wherein the composition includes a polynucleotide that hybridizes to a complement of the polynucleotides under stringent conditions, the label on said container indicates that the composition can be used to evaluate the presence of a molecular signature in at least one type of mammalian cell, and instructions for using the polynucleotide for evaluating the presence of biomolecule RNA or DNA in at least one type of mammalian cell.

Other optional components in the kit include, microarrays, one or more buffers (e.g., block buffer, wash buffer, substrate buffer, etc), other reagents such as substrate (e.g., chromogen) which is chemically altered by an enzymatic label, epitope retrieval solution, control samples (positive and/or negative controls), control slide(s) etc.

The invention has been described in detail with reference to preferred embodiments thereof. However, it will be appreciated that those skilled in the art, upon consideration of this disclosure, may make modifications and improvements within the spirit and scope of the invention. The following non-limiting examples are illustrative of the invention.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Embodiments of the invention may be practiced without the theoretical aspects presented. Moreover, the theoretical aspects are presented with the understanding that Applicants do not seek to be bound by the theory presented.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

Materials and Methods:

Clinical Evaluation of Patients:

Transcriptomic analysis of heart tissue was performed in matched cohorts of patients with IDCM (n=32) and myocarditis (n=16) selected from a biorepository containing samples from patients with new onset heart failure (HF; n=350). Patients underwent EMB as part of a comprehensive diagnostic evaluation of heart dysfunction that included history and physical exam, right-heart cardiac catheterization and echocardiography. All patients with history suggestive for ischemic heart disease or at least two standard risk factors for atherosclerosis were further evaluated with coronary angiography. Blood tests were performed for cardiac enzymes, thyroid-function and antinuclear antibodies.

Four to six biopsy specimens were obtained from each patient and examined by an experienced cardiac pathologist. In addition to standard staining, Congo red was used to identify amyloidosis and Prussian blue if hemochromatosis was suspected. Myocarditis was defined according to Dallas criteria, without additional tests for presence of viral RNA, such as PCR.

After this extensive evaluation, idiopathic dilated cardiomyopathy (IDCM) was a diagnosis of exclusion. In addition to diagnostic biopsies, one sample was flash frozen and stored in liquid nitrogen for microarray analysis. All participants gave written informed consent for collection of samples and clinical data. Right ventricular septal EMBs were obtained by advancing a disposable bioptome (Argon; Jawz) via the right jugular vein under fluoroscopic guidance.

Selection of Patients:

A total of 75 samples were used for microarray analysis. Forty-eight samples were selected for the first transcriptomic study. These included samples from patients with myocarditis (n=16) defined by the Dallas criteria and idiopathic dilated cardiomyopathy (IDCM, n=32) selected in a case-control fashion based on age, gender, functional parameters from echocardiography and right heart catheterization, and medication usage. In addition, samples from 6 patients were identified with myocarditis with divergent baseline criteria, from which the diagnostic accuracy of the biomarker was independently tested. Finally, RNA was prepared from samples obtained from patients with rare but clinically significant variants of inflammatory heart disease—cardiac sarcoidosis (n=9), giant cell myocarditis (n=3), peripartum cardiomyopathy (n=6), and heart failure in the setting of systemic lupus erythematosus (n=3).

RNA Extraction and Microarray Hybridization:

Total RNA was extracted from biopsies as previously described. Quality control of integrity of RNA was performed with the 2100 Bioanalyzer (Agilent). MIAME guidelines were followed for all steps of the procedure. The extracted RNA (average 568±88 ng; Standard Error of the Mean (SEM)) was preprocessed with the Ovation Biotin RNA Amplification and Labeling System (NuGen, Cat. No. 2300-12) for subsequent hybridization with the Human Genome U133 Plus 2.0 Array from Affymetrix without additional amplification step.

Bioinformatic and Biostatistic Software:

Microarray data was normalized with Robust Multiarray Average (RMA) and analyzed with Significance Analysis of Microarrays (SAM) to identify differentially expressed genes in patients with myocarditis (n=16) vs IDCM (n=32). The resulting gene list was further processed with Meta Core pathway analysis incorporated in GeneGo (bioinformatics software, St. Joseph, Mich.). Organ- and species-specific pre-filtering was performed before network analysis, in order to extract solely pathways that are truly interrelated in the human heart. Each network was provided with a p-value, using the basic formula for hypergeometric distribution. This formula provides a value that represents the probability for a particular mapping of an experiment to a map (or network/process) to arise by chance, considering the numbers of genes in the experiment vs the number of genes in the map within the "full set" of all genes on maps.

In addition, a z-score was calculated for each network, which reflects the saturation with genes from the experiment. A high z-score indicates a network that contains a large amount of genes from the experiment.

In order to determine the minimum number of differentially expressed genes required for detection of patients with myocarditis compared to IDCM, Prediction Analysis of Microarrays (PAM) was used to obtain a biomarker based upon a nearest shrunken centroid. The classifier was developed from a train set (n=33), consisting of ⅔ of data, and applied to an independent test set (n=15) containing ⅓ of data.

After developing the transcriptomic biomarker with a case-control design, its performance was tested in unmatched samples, to test its generalizability independent of age, gender, heart function or drug therapy. To test this hypothesis, samples from patients with myocarditis (n=6) were used, who presented with higher ejection fractions (65±4.7%). Finally, the molecular signature was illustrated as a heatmap by an unsupervised hierarchical clustering approach in R based on Euclidean distance.

Then PAM was used to identify molecular signatures in samples from patients with giant cell myocarditis (n=3), sarcoidosis (n=9), peripartum cardiomyopathy (n=6) and systemic lupus erythematosus (n=3), which distinguish them both from IDCM as well as myocarditis and further refine diagnosis between sarcoidosis and giant cell myocarditis.

In order to test, if previously established classification algorithms can further reduce the number of genes necessary for accurate prediction, misclassification-penalized posteriors classification (MiPP) were applied, which successfully predicts rejection in liver transplant recipients. The MiPP package is an application in the R environment, which employs the libraries MASS for lda/qda (linear/quadratic discriminant analysis and e1071 for SVM (support vector machine). This software sequentially adds genes to a classification model based upon the Misclassication-Penalized Posteriors principle, which takes into account the likelihood that a sample belongs to a given class by using posterior probability of correct classification.

First MiPP was used to test several different classification rules, to further reduce the novel molecular signature, consisting of 62 genes. Support vector machine was subsequently applied with radial basis function (SVM-rbf) and lineal function (SVM-lin), quadratic discriminant analysis (qda), linear discriminant analysis (lda) and a combination of lda, qda and svm-rbf. When support vector machine algorithms are used for classification, the input data is plotted as two vectors in an n-dimensional space and a virtual hyperplane is created that best separates the two phenotypes. This hyperplane is then used to classify samples with unknown phenotypes. Linear discriminant analysis uses a linear combination of features, which best separate two or more classes. Quadratic discriminant analysis is closely related to lda, however there is no assumption that the covariance of each of the classes is identical. Models were developed based upon 5-fold cross validation in a train set (⅔ of data) and subsequent validation in an independent test set (⅓ of data).

In order to evaluate, if distinct models are generated from additional random splits, 50 random divisions were performed to develop individual classification models, which were then validated in 200 independent splits. As an additional confirmatory test, principal components analysis (PCA) was performed to illustrate how well patients with myocarditis can be separated from patients with IDCM based on the original 62 genes molecular signature, and to test if genes that were identified by MiPP analysis to be the most robust classifiers, would also be discovered to be important when PCA was applied. PCA is a method that depicts the importance of genes for phenotypic classification by means of illustration through Eigen vectors towards a phenotype, in which the gene is overexpressed. If genes are less robust as classifiers, the corresponding vector directs towards the center with close to vertical direction. Important classifiers are depicted with vectors having endpoints far from the center.

Further Testing of the Diagnostic Biomarker for Myocarditis in a Previously Published Data Set:

In order to test, if the developed transcriptomic diagnostic biomarker enables detection of myocarditis in entirely independent samples, that were collected and processed at a different time point, a previously published dataset derived from patients with either giant cell myocarditis (n=3) or normal heart (n=11) and processed with the previous U133A microarray (Affymetrix) was used.

Validation of Microarrays with Quantitative Realtime RT-PCR:

Validation with realtime RT-PCR was performed in a randomly selected subset of patients (IDCM: n=10, myocarditis: n=10), with triplicates replication. First-strand cDNA was synthesized with a High-Capacity cDNA Reverse-Transcription Kit (Applied Biosystems Inc., CA, USA) from 100 ng total RNA, which was amplified with MessageAmp II Amplification Kit (Applied Biosystems Inc., CA, USA). TaqMan probes, labeled with 6-carboxyfluorescein (FAM) were designed for a subset of differentially expressed genes identified by microarray analysis: CD14, FCERIG, TLR1, TLR2, TLR7, ITGB2, SIGLEC1, ADCY7, MEGF9, PTPLAD1, SWAP70, MSI1, LCE1E and HLA-DQ1, as well as the housekeeping gene 18S RNA. Data were analyzed by the threshold cycle (Ct) relative-quantification method (error bars=mean standard error).

Example 1: Diagnostic Transcriptomic Biomarkers in Inflammatory Cardiomyopathies Table 13 depicts the baseline clinical variables of patients included in the initial case-control population with idiopathic dilated cardiomyopathy (IDCM) and Dallas criteria defined lymphocytic myocarditis. By design, there were no differences in gender, age, functional parameters or medication between the two groups.

Discovery of Phenotype Specific Differences in Gene Expression and Involved Pathways:

To identify differential gene expression between patients with IDCM (n=32) and those with lymphocytic myocarditis (n=16), oligonucleotide microarrays were used to analyze RNA obtained from endomyocardial biopsies (EMBs) from affected patients at first presentation with new onset heart failure. 9,878 differentially expressed genes (q<5%, fold change (FC)>1.2) were identified in patients with IDCM compared to myocarditis (FIG. 1). Transcripts with FC>2 (141 over-expressed and 16 down-regulated transcripts) are provided as in Tables 13 and 14. Pathway analysis with GeneGo Metacore revealed overexpression of a total of 8 networks in myocarditis vs IDCM (Table 3). No specific networks were revealed within the small amount of down-regulated transcripts with FC>2 (16 genes).

Figure 2:
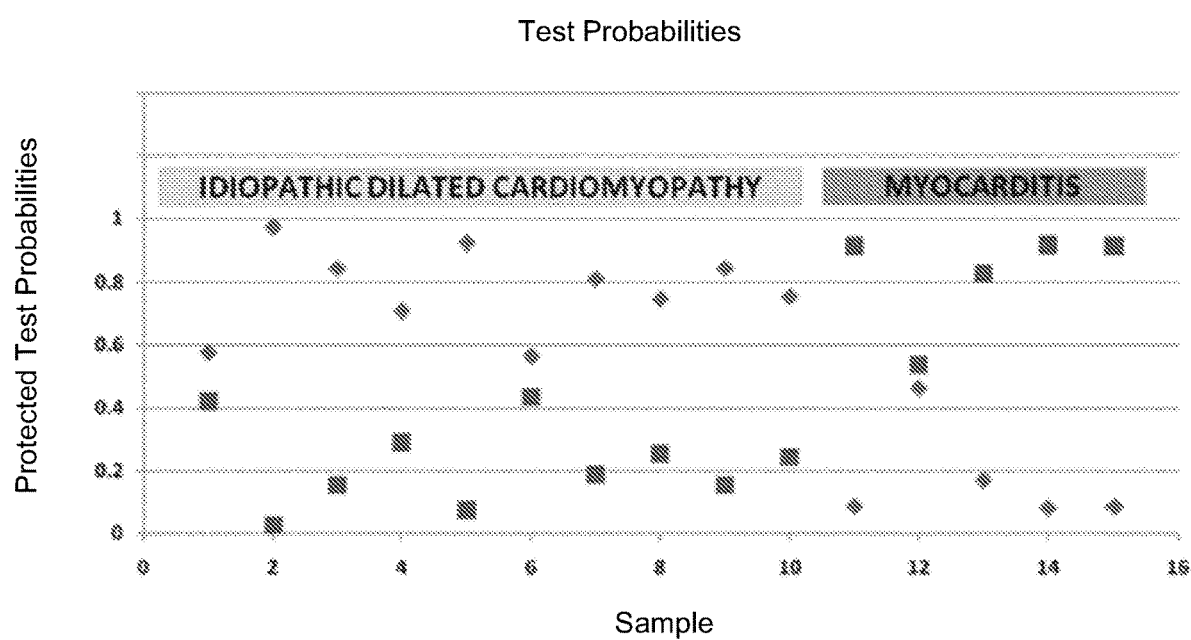
FIG. 2: Validation of a 62-gene molecular signature in an independent test set (idiopathic dilated cardiomyopathy: n=10, myocarditis: n=5) using Prediction Analysis of Microarrays (PAM): The y-ordinate illustrates the predicted test probability values obtained from PAM analysis; x-ordinate lists the number of samples. While samples were assigned to different classes with varying probability values, the classification accuracy of the transcriptomic biomarker was 100%.
Figure 3:
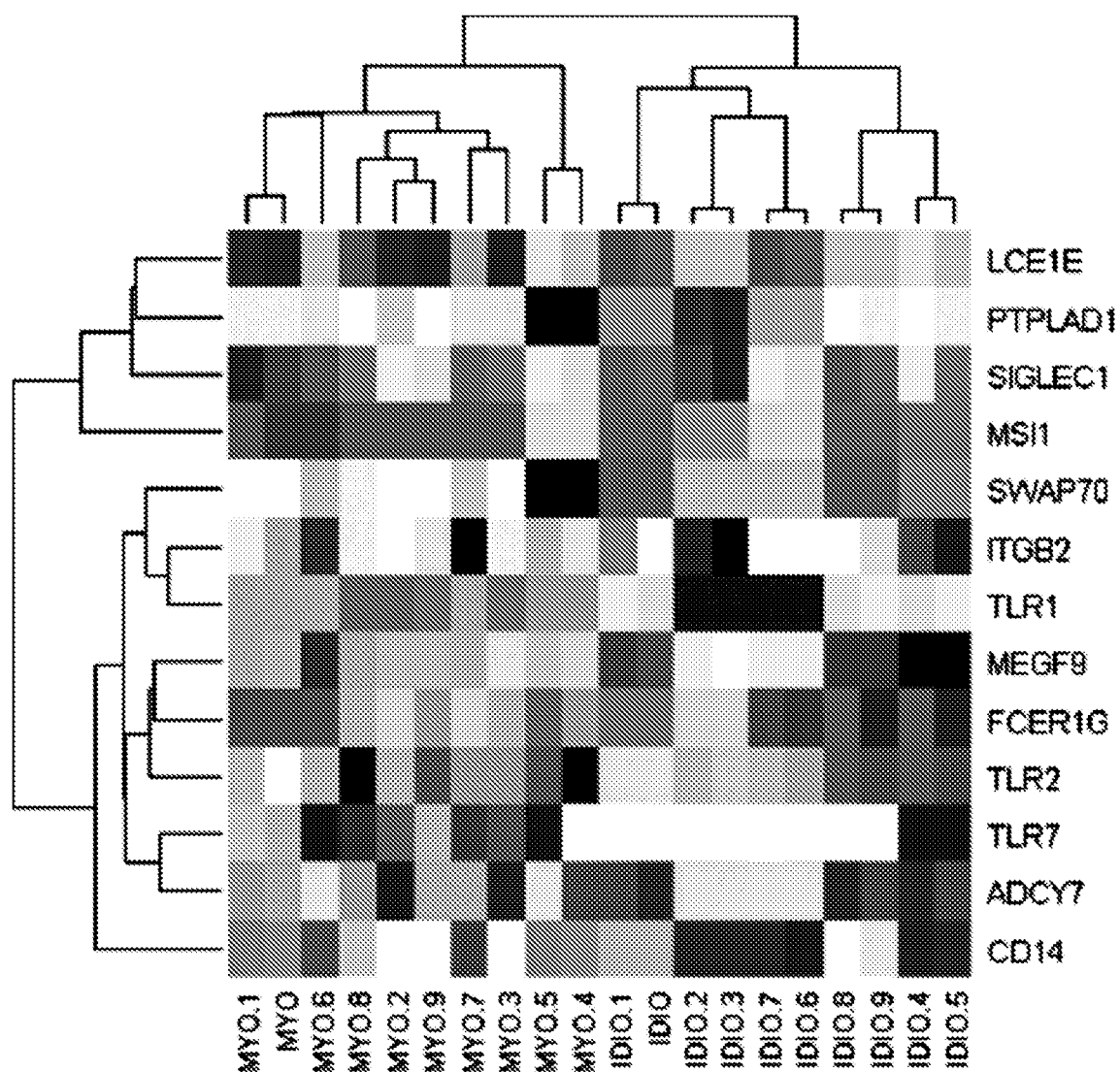
FIG. 3: Distinction of patients with idiopathic dilated cardiomyopathy vs lymphocytic myocarditis based on results from quantitative realtime RT-PCR: This heatmap was created with an unsupervised clustering approach based on Euclidean distance in R, using the detected gene expression levels from quantitative realtime RT-PCR as confirmatory test. Columns represent samples and rows represent genes labeled with their corresponding gene symbol. Application of the developed 13 genes molecular signature through realtime RT-PCR correctly identified all samples.

Identification of a Molecular Signature to Distinguish Myocarditis from Non-Inflammatory Cardiomyopathy Patients:

Prediction analysis of microarrays (PAM) were applied in a training set containing ⅔ of data (IDCM: n=22; myocarditis: n=11) and evaluated its accuracy in an independent test set, containing ⅓ of data (IDCM: n=10; myocarditis: n=5). The developed transcriptomic diagnostic biomarker consisted of a minimal set of 62 transcripts (Table 14). When the molecular signature was tested in the matched independent samples (n=15), it performed with 100% accuracy (sensitivity: 100%, 95 CI: 46-100%; specificity: 100%, 95 CI: 66-100%; positive predictive value, PPV: 100%, 95 CI: 46-100%; negative predictive value, NPV: 100%, 95 CI: 66-100%; FIG. 2). All samples were predicted correctly, independent of the degree of inflammation—borderline or active myocarditis.

Next, the transcriptomic diagnostic biomarker was tested in an additional set of independent samples derived from patients with myocarditis (n=6), who presented with higher ejection fractions (65±4.7%), compared to the case-control samples. In this group, the molecular signature still had a high degree of diagnostic accuracy and identified 83% of patients with myocarditis correctly (sensitivity: 91%, 95 CI: 57-100%; specificity: 100%, 95 CI: 66-100%; PPV: 100%, 95 CI: 66-100%; NPV: 91%, 95 CI: 57-100%).

Additional Identification of Gene Models with Recently Established Classification Strategies:

In order to obtain a more parsimonious molecular signature several bioinformatic approaches were employed, followed by quantitative realtime RT-PCR validation. First, multiple established classification algorithms were applied using the MiPP package in R that includes lineal discriminant analysis (lda), quadratic discriminant analysis (qda), supervector machine with radial basis function (svm-rbf), and supervector machine with lineal function as kernel (svm-lin). When applied to the 62 gene signature, these algorithms revealed that a 4 gene subset signature would be diagnostic. Table 15 contains the mean error for each established set of genes developed by individual rules or combination of rules. Using these algorithms, a highly diagnostic set of four genes (mean error of 0.167 in independent validation sets (n=18)).

Since this was a random split into train and test set, this analysis was continued by testing if a different random split of data would reveal distinct models. Splitting of data into train (⅔) and test set (⅓) and selecting a model for a given split were repeated 50 times. For each split, the parsimonious model identified was further evaluated by 200 independent splits. KRT78, MSI1, POU4F1, LCE1 and the EST 1556507_at were selected as top classifiers, with a mean error of 0.086 after validation in 200 independent splits (table 16). Mean sMiPP is an additional measure for performance of a given gene model, approximating 1 with increasing accuracy. When the top 5 gene models (Table 16) were validated in 200 independent random splits, a mean sMiPP was obtained ranging from 0.776-0.791 (Table 16). Since those models were built from 50 initial random splits, it is likely that identical gene clusters are identified in subsequent splits, as it occurred in this analysis (Table 16: split #17 and split #45).

Figure 4A:
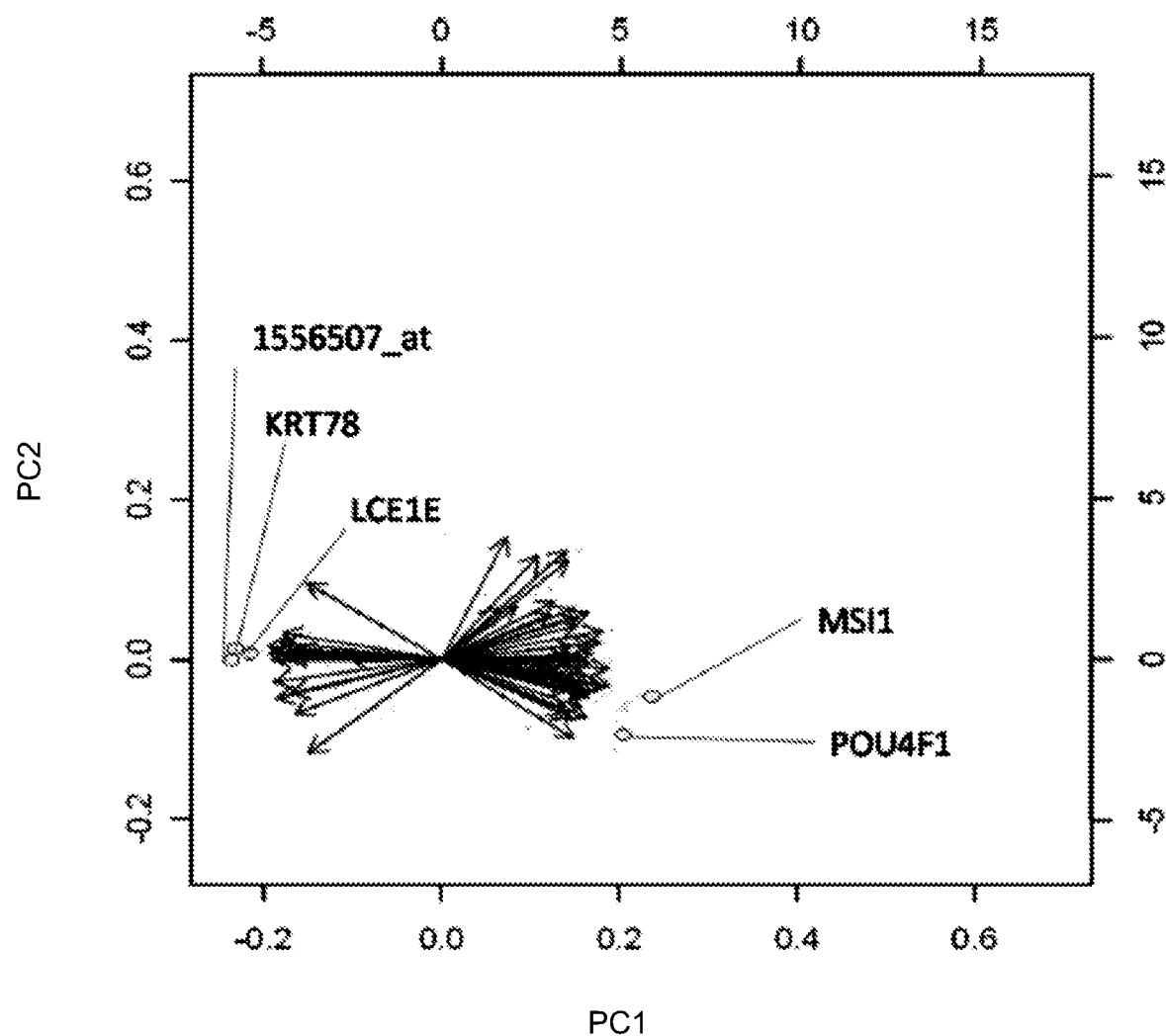
FIGS. 4A-4B: Principal Components Analysis (PCA) of patients with myocarditis vs idiopathic dilated cardiomyopathy (IDCM): To illustrate significance of each of the 62 genes for phenotypic categorization, PCA was performed with correlation matrix in samples from patients with myocarditis (n=16) or IDCM (n=32) with genes as variables. Genes are labeled with serial numbers and expression levels of each individual gene are illustrated as Eigen vector towards the class, in which they are overexpressed. Vectors close to the center with close to vertical direction depict genes that were less robust, while genes that were highly specific for a phenotype were illustrated as vectors with endpoint distant from the center directing towards the corresponding clustered set of samples of a specific phenotype. A) Clustered samples from patients with myocarditis are labeled "M", while IDCM samples are labeled "I". All samples from myocarditis, except two, were noticeably grouped together, suggesting that a small set of 62 genes enables clear distinction between patients with inflammatory heart disease and IDCM. Importantly, those two samples were also misclassified in the heatmap analysis, while Prediction Analysis of Microarrays identified both of them correctly. B) Encircled are genes that were repeatedly identified to be the most robust markers of myocarditis, when various algorithms of Misclassified-Penalized Posterior classification were applied. Output from PCA places those genes both far from the center as well as distant from the vertical line, confirming that these are highly robust classifiers for myocarditis.
Figure 4B:
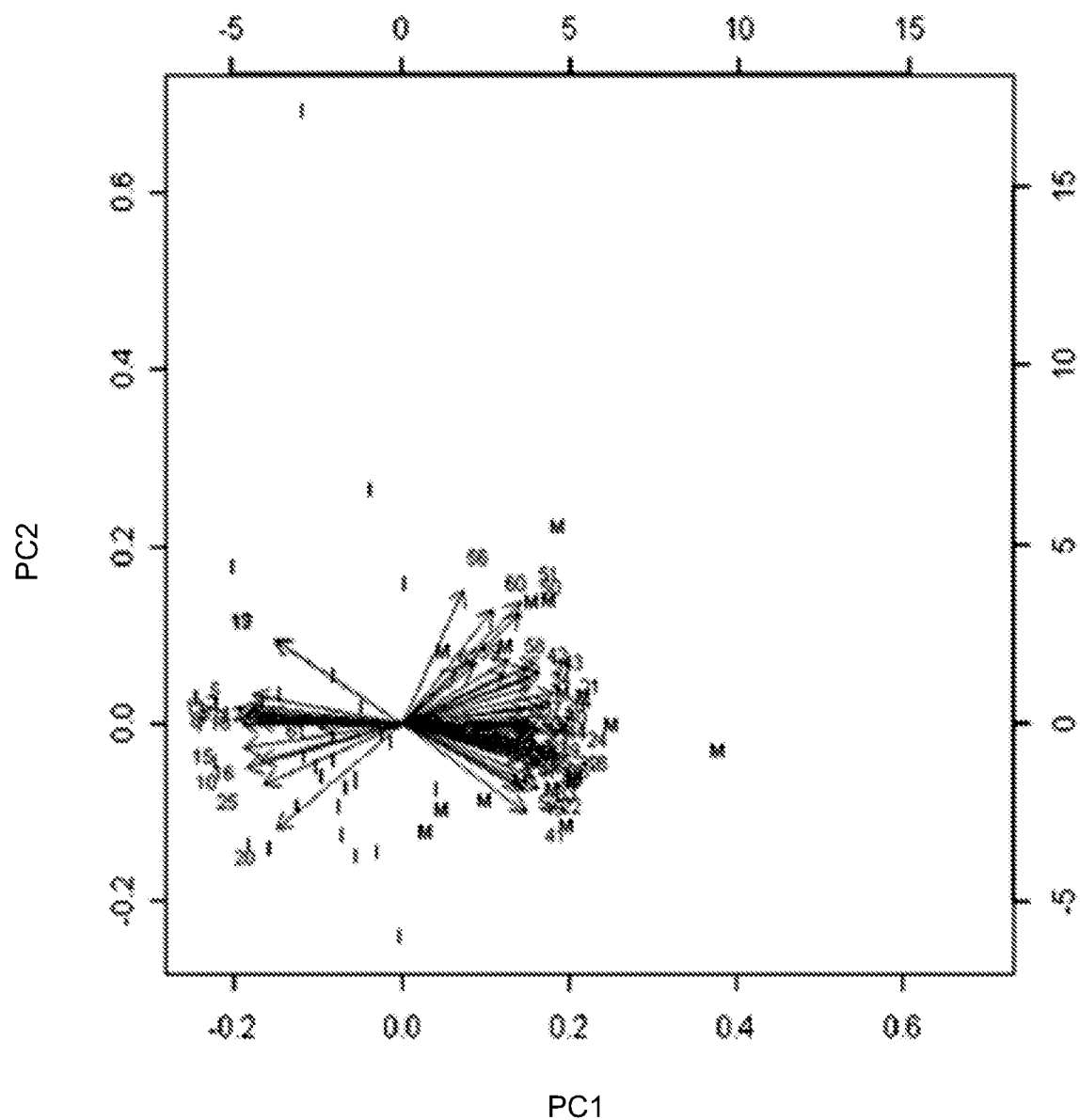

Validation of Significance of Genes for Phenotypic Characterization by Principal Components Analysis (PCA):

PCA is a valuable tool to illustrate importance of individual genes for classification of their corresponding phenotype. In agreement with results from the MiPP analysis, the transcripts 1556507_at, KRT78, LCE1E, MSI1 and POU4F1 were identified as highly important, with vectors having their endpoints distant from the center (FIG. 5A). Additional genes that were revealed to be highly robust were ITGB2, HERC6, ADCY7, NEK3, MEGF9, as well as the ESTs 1558605 at and 1565662 at. In addition, PCA clustered patients with similar expression patterns as one principal component (PC). As visible in FIG. 4B, samples from patients with myocarditis noticeably separated from patients with IDCM.

Validation of Transcriptomic Data with Quantitative Realtime RT-PCR:

To obtain technical validation of the results from microarray analysis, realtime RT-PCR was performed on a subset of 16 genes (Table 17). Genes were selected from the resulting gene lists of the bioinformatic approach, based on biological plausibility and robustness as classifiers for lymphocytic myocarditis.

This approach confirmed overrepresentation of HLA-DQ1+ patients in myocarditis (60%), while only 20% of patients with IDCM were positive for DQ1. Fold change (FC) of most genes measured by quantitative realtime RT-PCR strongly correlated with data obtained from microarray analysis, except for MSI1, where realtime RT-PCR data revealed much stronger downregulation in patients with myocarditis vs lymphocytic cardiomyopathy than obtained from the microarray data. Genes that were revealed by realtime RT-PCR to have highest fold changes were CD14 (FC=+6.8), FCER1G (FC=+5), TLR1 (FC=+4.2), TLR2 (FC=+5.9), SIGLEC1 (FC=+4.3) and ADCY7 (+4.2) (Table 17). However, among the 4 genes that were revealed by MiPP analysis, KRT78 and POU4F1 could not be confirmed with realtime RT-PCR. Since KRT78 appeared highly robust as classifier based on the microarray results, two different primer pairs were used to detect either the 3' or the 5' end of the gene sequence. However, none of them were able to detect KRT78 in any of the samples. When total RNA was used from immortalized keratinocytes as a positive control, a signal was received from each primer pair. In order to exclude the possibility of cross-hybridization that may have occurred on the microarray assay, a batch search in the NCBI database (blast.ncbi.nlm.nih.gov/Blast.cgi) of the target sequence that was used on the Affymetrix chip. However, there was no significant sequence homology with any gene other than KRT78. Despite this minimal incoherence between microarray analysis and the more specific realtime RT-PCR, the diagnostic biomarker was minimized to a very small set of 13 genes that performed highly robust with both methods (100% sensitivity, 100% specificity). When applied to a subset of myocarditis patients with higher ejection fraction, the 13 gene signature performed with a sensitivity of 75% (95CI: 36-96%), specificity of 100% (95CI: 52-100%), PPV of 100%/(95CI: 52-100%) and NPV of 75%(95CI: 36-96%).

Subtyping of Inflammatory Cardiomyopathies with Diagnostic Transcriptomic Biomarkers:

It was then sought to test if rare subtypes of inflammatory cardiomyopathy can be distinguished from IDCM using TBBs. Molecular signatures containing 8 to 56 genes were identified that identified patients with (a) giant cell myocarditis (n=3), (b) sarcoidosis (n=9) and (c) peripartum cardiomyopathy (n=9) with very high accuracy (up to 86%, Table 18). Further it was sought to test the possibility of refining the diagnosis within the group of inflammatory cardiomyopathies and to distinguish these rare disorders from the more common lymphocytic myocarditis. While patients with giant cell myocarditis and sarcoidosis each contained a very robust cluster of genes, with an overall accuracy of 92% and 94% respectively, peripartum cardiomyopathy appeared to be less distinct in its transcriptome with a molecular signature that performed only with 69% overall accuracy (Table 19), likely reflecting a spectrum of etiologies of this condition. Gene lists of each classifier are provided in Tables 5-11.

After obtaining these compelling results, it was sought to evaluate, if diagnosis between sarcoidosis and giant cell myocarditis, two subtypes of inflammatory cardiomyopathy that strongly resemble each other by histology, could be further refined. A molecular signature was developed that identified patients with giant cell myocarditis vs sarcoidosis based on a classifier of 19 genes with 67% sensitivity (95 CI: 13-98%), 75% specificity (95 CI: 36-96%), PPV of 50% (95 CI: 9-91%) and NPV of 86% (95 CI: 43-99%; Table 12).

DISCUSSION

Distinction of inflammatory as compared to non-inflammatory cardiomyopathies by standard histology has, prior to this study, represented a major diagnostic challenge. Moreover, delineating between different inflammatory cardiomyopathies with highly variable clinical courses has been, prior to this study, an even more challenging task. Given the emerging value of transcriptomics to add greatly to the accuracy of complex diagnoses, this approach was applied to the problem of diagnostic inaccuracy in inflammatory diseases of the heart, and here in, report the success with this approach.

Inflammatory disorders of the heart have been, prior to this study, notoriously difficult to diagnose due to the patchy nature of the inflammation. In addition, a wide variety of underlying inflammatory conditions, with highly variable clinical outcomes, can affect the heart. Here the transcriptome obtained from a single endomyocardial biopsy was employed to develop biomarkers that enhanced the diagnostic accuracy for detection of cardiac inflammation as well at the ability to separate between important subtypes of cardiac inflammation. This approach illustrated the value of the transcriptome as a diagnostic biomarker for heart diseases and offers insights into a new clinically useful tool. The data herein evidence the results obtained using the TBBs to distinguish between idiopathic and ischemic cardiomyopathy and to predict long term prognosis in new onset dilated cardiomyopathy.

The discoveries reported here are clinically relevant as high diagnostic sensitivity in cardiomyopathy facilitates the appropriate use of new myocarditis specific therapies. Early and accurate diagnosis in this condition is essential so as to avoid excessive myocardial damage resulting from failure to apply therapies. New candidate therapies for myocyarditis include anti-inflammatory cytokines, anti-viral agents, and immunoabsorption. In this regard, IFN therapy has been safely applied in humans, leading to increased LV function and elimination of viral infection. Immunoglobin administration in acute myocarditis as well as application of Ca-channel blockers, are potential approaches with promising preliminary data that entail further evaluation. While the use of immunosuppression in inflammatory cardiomyopathy is highly controversial, there is growing consensus that the identification of the relevant subtype of inflammatory cardiomyopathy is crucial for successful treatment. Accurate diagnosis is also critical for prognostic assessment, since clinical outcome in inflammatory cardiomyopathies correlates with disease etiology. TBBs add valuable information to a comprehensive diagnostic evaluation of new onset heart failure.

In order to achieve an accurate biomarker a broad range of bioinformatic approaches were employed. These included SAM, PAM, MiPP, unsupervised hierarchical clustering and PCA. Using SAM, a large number of differentially expressed genes in patients with lymphocytic myocarditis vs idiopathic dilated cardiomyopathy were identified. Importantly, differentially expressed genes involved multiple biological networks with inflammatory components. Using these differentially expressed genes, a subset were identified that functioned as a highly accurate biomarker, performing with perfect accuracy, using nearest shrunken centroids.

To find the smallest set of genes for classification, SVM-rbf, SVM-lin, QDA, LDA and a combination of LDA, QDA and SVM-rbf in MiPP were used. Overall, all rules applied in MiPP consistently revealed 4 genes that were highly robust classifiers, and these genes were further confirmed using PCA. Interestingly, two of the four "robust" predictive genes were not found to be present when quantitative realtime RT-PCR was used to probe the RNA sample. Finally a highly parsimonious biomarker was developed herein, using MSI1 and LSI1 in combination with a subset of biologically relevant genes present in the PAM-derived 62 gene TBB, as well as from SAM analysis and evaluated this signature using realtime RT-PCR; the 13 gene signature performed with perfect accuracy to identify samples in the independent test set of this case-control study. The observation that mean fold changes obtained from realtime RT-PCR were not entirely identical with the results from SAM analysis underlines the strength of molecular signature analysis for the development of biomarkers, a classification strategy that emphasizes differentially expressed gene expression patterns rather than individual genes. Since the expression level of an individual gene may vary across a population that shares the same phenotype, the overexpression or downregulation of an entire cluster of genes is more specific for a disease.

Based on these findings, it was concluded that both the transcriptomic biomarker derived from PAM analysis, as well as the parsimonious molecular signature that resulted from multiple classification algorithms and testing for biological plausibility, performed highly accurately and should be a clinically valuable tool for the detection of myocarditis. While the more comprehensive biomarker of 62 genes performed with slightly higher accuracy, the 13 genes molecular signature is more practical for clinical application.

Since the original dataset was established by the inventors in which the TBB was developed and was matched in a case-control fashion, it was further evaluated if the molecular signature is generalizable, or if it is possibly overfit to this particular study design. It has been shown in the past that confounding factors such as gender, age and therapy can affect gene expression. When the TBB was applied in an additional validation set containing samples from patients with an average EF that was twice as high as the average EF of the original data set (65 vs 30%), the biomarker performed with almost perfect accuracy.

Both molecular signatures will go into testing in a phase I clinical trial, to further evaluate the diagnostic value of those biomarkers in comparison to a combination of current diagnostic tools, such as MRI, EKG, cardiac enzymes, viral screening and auto-heart antibodies. Most likely, its addition to current diagnostic standards will dramatically increase sensitivity for myocarditis. The ability to detect inflammatory components, such as involvement of the complement cascade or genes involved in cell adhesion such as ITGB2 by microarray analysis may explain why this technology is able to identify myocarditis with much greater sensitivity at an earlier stage than standard histology, a method that requires presence of inflammatory cells.

This study also addressed subtyping of inflammatory cardiomyopathies. While the sample size of rare cardiomyopathies was too small to finalize a minimal set of genes for clinical application, it reveals highly robust molecular signatures that distinguish patients with giant cell myocarditis, sarcoidosis, and systemic lupus erythematosus noticeably from lymphocytic myocarditis and IDCM. Interestingly, classification of peripartum cardiomyopathy was less accurate, most likely because of multiple factors interacting in this type of disease, ranging from nonspecific changes such as replacement fibrosis to lymphocytic infiltration.

The findings herein, that patients with giant cell myocarditis share a gene expression profile that is highly distinct from patients with cardiac sarcoidosis and that enables distinction based on a single EMB, has important clinical implications. Due to high histopathological similarity between giant cell myocarditis and sarcoidosis, it may be that giant cell myocarditis may be a subtype of the spectrum of cardiac sarcoidosis. Here it was shown that these types of cardiomyopathy are clearly distinct from each other on the molecular level. Importantly, one of the differentially expressed genes in giant cell myocarditis vs sarcoidosis was FCER1A, which has positive regulatory function in type 1 hypersensitivity. While this finding may help in the future to understand pathophysiology of these rare, but clinically important diseases, the ability to distinguish patients with giant cell myocarditis from sarcoidosis has high clinical relevance for risk assessment. Transplant-free survival is substantially greater in cardiac sarcoidosis than in giant cell myocarditis, and giant cell myocarditis may respond to treatment with monoclonal antibodies against the CD3 receptor.

While the main goal of this study was to develop a highly accurate biomarker to distinguish lymphocytic myocarditis from IDCM, these results also provided insight into disease pathophysiology on the molecular level. Among overexpressed genes in myocarditis was CD8, involved in inflammation and binding and reported to play a fundamental role in myocarditis. Surprisingly, a pathway involving the TSH receptor was overexpressed in patients with myocarditis, implicating potential pathophysiologic overlap with inflammatory thyroid disease, a finding clinically established for giant cell myocarditis (Graves'). There was overrepresentation of patients, positive for the HLA-DQ1B locus in myocarditis vs IDCM, suggesting possible susceptibility for lymphocytic myocarditis in this group. Many transcripts, involving structural proteins and muscle development (late cornified envelope 1 E, collagen type I), were downregulated in myocarditis, possibly explaining structural defects and consequent dilatation in patients with this type of disease.

In short, a transcriptomic diagnostic biomarker was discovered herein, derived from a single EMB, which identified samples with lymphocytic myocarditis with very high accuracy. These findings are highly relevant for a clinical application, since this novel diagnostic tool exceeds sensitivity and specificity of any technology that has been applied previously. The molecular signature was highly robust and replicated multiple times by a broad set of established classification algorithms. Validation in two independent data sets revealed high diagnostic accuracy and genes within the transcriptomic biomarker suggest biological plausibility. Altogether, using this approach dramatically increases the diagnostic accuracy of a single EMB, which may be of critical importance to the development and allocation of emerging specific therapies for inflammatory conditions of the heart.

TABLE 1

Overexpressed genes in patients with myocarditis vs idiopathic dilated cardiomyopathy (q < 5%, FC > 2) and their biological function

| Probe Set ID | Gene Symbol | Gene Title | GO biological process term |
| --- | --- | --- | --- |
| 1552302_at | FLJ77644, TMEM106A | similar to transmembrane protein 106A | NA |
| 1552553_a_at | NLRC4 | NLR family, CARD domain containing 4 | apoptosis, caspase activation, defense response to bacterium, interleukin-1 beta secretion |
| 1552584_at | IL12RB1 | interleukin 12 receptor, beta 1 | cell surface receptor linked signal transduction, positive regulation of cell proliferation |
| 1554899_s_at | FCER1G | Fc fragment of IgE, high affinity I, receptor for; gamma polypeptide | positive regulation hypersensitivity, phagocytosis, engulfment, immunoglobulin mediated immune response, positive regulation of interleukin-6 and 10 and TNF production, positive regulation of mast cell cytokine production |
| 1555349_a_at | ITGB2 | integrin, beta 2 (complement component 3 receptor 3 and 4 subunit) | apoptosis, inflammatory response, cell adhesion, leukocyte adhesion, integrin-mediated signaling pathway |
| 1559584_a_at | C16orf54, hCG_1644884 | chromosome 16 open reading frame 54 | NA |
| 1563245_at | MGST1 | microsomal glutathione S-transferase 1 | glutathione metabolic process |
| 1565162_s_at | ANXA2 | annexin A2 | skeletal development |
| 1568126_at | SPP1 | Secreted phosphoprotein 1 | ossification, cell adhesion |
| 1568574_x_at | IFI30 | interferon, gamma-inducible protein 30 | oxidation reduction |

TABLE 1-continued

Overexpressed genes in patients with myocarditis vs idiopathic dilated cardiomyopathy (q < 5%, FC > 2) and their biological function

| Probe Set ID | Gene Symbol | Gene Title | GO biological process term |
| --- | --- | --- | --- |
| 201422_at | CTSC | cathepsin C | proteolysis, immune response |
| 201487_at | LAPTM5 | lysosomal multispanning membrane protein 5 | transport |
| 201721_s_at | CD14 | CD14 molecule | response to molecule of bacterial origin, phagocytosis, apoptosis, inflammatory response |
| 201743_at | CAPG | capping protein (actin filament), gelsolin-like | protein complex assembly, cell projection biogenesis |
| 201850_at | PLTP | phospholipid transfer protein | lipid metabolic process, transport |
| 202075_s_at | VAMP8 | vesicle-associated membrane protein 8 (endobrevin) | vesicle-mediated transport |
| 202546_at | LYN | v-yes-1 Yamaguchi sarcoma viral related oncogene homolog | protein amino acid phosphorylation, intracellular signaling cascade, positive regulation of cell proliferation, response to hormone stimulus, erythrocyte differentiation, interspecies interaction between organisms |
| 202625_at | ITGB2 | integrin, beta 2 (complement component 3 receptor 3 and 4 subunit) | apoptosis, inflammatory response, cell adhesion, leukocyte adhesion, integrin-mediated signaling pathway, neutrophil chemotaxis |
| 202803_s_at | PCK2 | phosphoenolpyruvate carboxykinase 2 (mitochondrial) | gluconeogenesis |
| 202847_at | CSF1R | colony stimulating factor 1 receptor | protein amino acid phosphorylation, signal transduction, transmembrane receptor protein tyrosine kinase signaling pathway, multicellular organismal development, cell proliferation |
| 203104_at | RASSF2 | Ras association (RalGDS/AF-6) domain family member 2 | cell cycle, signal transduction, negative regulation of cell cycle |
| 203185_at | RPS6KA1 | ribosomal protein S6 kinase, 90 kDa, polypeptide 1 | protein amino acid phosphorylation, signal transduction, protein kinase cascade |
| 203379_at | CD53 | CD53 molecule | signal transduction |
| 203416_at | PLEK | pleckstrin | intracellular signaling cascade |
| 203471_s_at | SEMA4D | sema domain, immunoglobulin domain (Ig), transmembrane domain (TM) and short cytoplasmic domain, (semaphorin) 4D | NA |
| 203528_at | CD163 | CD163 molecule | acute-phase response, inflammatory response |
| 203645_s_at | PLA2G2A | phospholipase A2, group IIA (platelets, synovial fluid) | phospholipid metabolic process, lipid catabolic process |
| 203649_s_at | CXCL9 | chemokine (C-X-C motif) ligand 9 | chemotaxis, defense response, inflammatory response, cellular defense response, G-protein coupled receptor protein signaling pathway |
| 203915_at | CYBB | cytochrome b-245, beta polypeptide | superoxide metabolic process, ion transport, inflammatory response, superoxide release, innate immune response |
| 203923_s_at | IRF8 | interferon regulatory factor 8 | transcription, immune response, myeloid cell differentiation |
| 204057_at | CD48 | CD48 molecule | defense response |
| 204118_at | TYROBP | TYRO protein tyrosine kinase binding protein | cellular defense response, intracellular signaling cascade |
| 204122_at | GLIPR1 | GLI pathogenesis-related 1 | NA |
| 204222_s_at | FCER1G | Fc fragment of IgE, high affinity I, receptor for; gamma polypeptide | positive regulation of hypersensitivity, positive regulation of interleukin-10 and 6 and tumor necrosis factor production, mast cell activation |
| 204232_at | PLEKHO2 | pleckstrin homology domain containing, family O member 2 | NA |
| 204436_at | CD44 | CD44 molecule | cell adhesion, cell-matrix adhesion |
| 204490_s_at | SLC7A7 | solute carrier family 7 (cationic amino acid transporter, y+ system), member 7 | amino acid metabolic process, transport |
| 204588_s_at | STC1 | stanniocalcin 1 | cellular calcium ion homeostasis, cell surface receptor linked signal transduction |
| 204595_s_at | CD52 | CD52 molecule | elevation of cytosolic calcium ion concentration, respiratory burst |
| 204661_at | VSIG4 | V-set and immunoglobulin domain containing 4 | negative regulation of interleukin-2 production, negative regulation of T cell proliferation |
| 204787_at | IL10RA | interleukin 10 receptor, alpha | NA |
| 204912_at | SASH3 | SAM and SH3 domain containing 3 | NA |
| 204923_at | TLR2 | toll-like receptor 2 | response to molecule of fungal origin, MyD88-dependent toll-like receptor signaling pathway, induction of apoptosis |
| 204924_at | CSTA | cystatin A (stefin A) | peptide cross-linking |
| 204971_at | CCR1 | chemokine (C-C motif) receptor 1 | chemotaxis, G-protein coupled receptor protein signaling pathway, response to wounding |
| 205098_at | LCP2 | lymphocyte cytosolic protein 2 (SH2 domain containing leukocyte protein of 76 kDa) | immune response, transmembrane receptor protein tyrosine kinase signaling pathway, mast cell activation, cytokine secretion |
| 205269_at | | | |
| 205270_s_at | GZMA | granzyme A (granzyme 1, cytotoxic T-lymphocyte-associated serine esterase 3) | proteolysis, apoptosis, cleavage of lamin, immune response, cytolysis |
| 205488_at | CD86 | CD86 molecule | immune response, positive regulation of cell proliferation, T cell activation |

TABLE 1-continued

Overexpressed genes in patients with myocarditis vs idiopathic dilated cardiomyopathy (q < 5%, FC > 2) and their biological function

| Probe Set ID | Gene Symbol | Gene Title | GO biological process term |
| --- | --- | --- | --- |
| 205685_at | CD8A | CD8a molecule | immune response, transmembrane receptor protein tyrosine kinase signaling pathway, T cell activation |
| 205758_at | ITGAM | integrin, alpha M (complement component 3 receptor 3 subunit) | cell adhesion, integrin-mediated signaling pathway |
| 205786_s_at | LY86 | lymphocyte antigen 86 | apoptosis, humoral immune response, cell proliferation |
| 205859_at | PTPN6 | protein tyrosine phosphatase, non-receptor type 6 | protein amino acid dephosphorylation, apoptosis, response to wounding |
| 206687_s_at | CCR2, FLJ78302 | chemokine (C-C motif) receptor 2 | chemotaxis, inflammatory response, cellular defense response, JAK-STAT cascade, interspecies interaction between organisms |
| 206978_at | PTPRC | protein tyrosine phosphatase, receptor type, C | negative regulation of T cell mediated cytotoxicity, positive regulation of B cell proliferation, defense response to virus |
| 207238_s_at | SYK | spleen tyrosine kinase | serotonin secretion, leukocyte adhesion neutrophil chemotaxis, interspecies interaction between organisms, positive regulation of interleukin-3 biosynthetic process, positive regulation of B cell differentiation, positive regulation of gamma-delta T cell differentiation, positive regulation of alpha-beta T cell differentiation |
| 207540_s_at | LILRB2 | leukocyte immunoglobulin-like receptor, subfamily B (with TM and ITIM domains), member 2 | immune response, cellular defense |
| 207697_x_at | LCP1 | lymphocyte cytosolic protein 1 (L-plastin) | actin filament bundle formation |
| 208885_at | CORO1A | coronin, actin binding protein, 1A | phagocytosis |
| 209083_at | HLA-DQB1 | major histocompatibility complex, class II, DQ beta 1 | antigen processing and presentation of peptide or polysaccharide antigen via MHC class II, immune response |
| 209480_at | DLK1 | delta-like 1 homolog (*Drosophila*) | multicellular organismal development |
| 209560_s_at | CD44 | CD44 molecule (Indian blood group) | cell adhesion, cell-matrix adhesion |
| 209835_x_at | SPP1 | secreted phosphoprotein 1 | ossification, cell adhesion |
| 209875_s_at | AIF1 | allograft inflammatory factor 1 | response to stress, inflammatory response, cell cycle arrest, negative regulation of cell proliferation |
| 209901_x_at | C3AR1 | complement component 3a receptor 1 | chemotaxis, inflammatory response, G-protein coupled receptor protein signaling pathway |
| 209906_at | CD300A | CD300a molecule | immune response, cell adhesion |
| 209933_s_at | NCF2 | neutrophil cytosolic factor 2 | cellular defense response |
| 209949_at | LILRB2 | leukocyte immunoglobulin-like receptor, subfamily B (with TM and ITIM domains), member 2 | immune response, cellular defense response, cell surface receptor linked signal transduction |
| 210146_x_at | TLR1 | toll-like receptor 1 | inflammatory response, macrophage activation, positive regulation of tumor necrosis factor biosynthetic process, positive regulation of interleukin-6 biosynthetic process |
| 210176_at | LAIR1 | leukocyte-associated immunoglobulin-like receptor 1 | immune response |
| 210644_s_at | LILRB1 | leukocyte immunoglobulin-like receptor, subfamily B (with TM and ITIM domains), member 1 | immune response, response to virus |
| 211336_x_at | TRBC1, TRBC2, TRBV19 | T cell receptor beta constant 1, T cell receptor beta constant 2, T cell receptor beta variable 19 | immune response |
| 211796_s_at | CD44 | CD44 molecule | cell adhesion, cell-matrix adhesion |
| 212063_at | PTPRC | protein tyrosine phosphatase, receptor type, C | negative regulation of T cell mediated cytotoxicity, cell surface receptor linked signal transduction, T cell differentiation, positive regulation of B cell proliferation, defense response to virus |
| 212587_s_at | | | |
| 212588_at | HLA-DQA1, HLA-DQA2 | major histocompatibility complex, class II, DQ alpha 1, major histocompatibility complex, class II, DQ alpha 2 | antigen processing and presentation of peptide or polysaccharide antigen via MHC class II |
| 212671_s_at | hCG_1998957, HLA-DQB1/B2, HLA-DRB1/2/3/4/5 | major histocompatibility complex, class II, DQ beta 1 and 2; DR beta 1, 2, 3, 4 and 5 | antigen processing and presentation of peptide or polysaccharide antigen via MHC class II |
| 212999_x_at | AIF1 | allograft inflammatory factor 1 | response to stress, inflammatory response, cell cycle arrest |
| 213095_x_at | DOCK2 | dedicator of cytokinesis 2 | actin cytoskeleton organization and biogenesis, lymphocyte chemotaxis |
| 213160_at | HSPA6 | heat shock 70 kDa protein 6 (HSP70B') | response to stress |
| 213418_at | RNASE6 | ribonuclease, RNase A family, k6 | RNA catabolic process, defense response |
| 213566_at | RAC2 | ras-related C3 botulinum toxin substrate 2 (rho family, small GTP binding protein Rac2) | chemotaxis, positive regulation of cell roliferation, regulation of respiratory burst |

TABLE 1-continued

Overexpressed genes in patients with myocarditis vs idiopathic dilated cardiomyopathy (q < 5%, FC > 2) and their biological function

| Probe Set ID | Gene Symbol | Gene Title | GO biological process term |
| --- | --- | --- | --- |
| 213603_s_at | MYO1F | myosin IF | NA |
| 213733_at | HLA-DQA1 | major histocompatibility complex, class II, DQ alpha 1 | antigen processing and presentation of peptide or polysaccharide antigen via MHC class II |
| 213831_at | LYZ | lysozyme (renal amyloidosis) | tRNA aminoacylation for protein translation, inflammatory response, defense response to bacterium |
| 213975_s_at | LOC648998 | similar to Neutrophil cytosol factor 1 (NCF-1) (Neutrophil NADPH oxidase factor 1) (47 kDa neutrophil oxidase factor) (p47-phox) (NCF-47K) (47 kDa autosomal chronic granulomatous disease protein) (NOXO2) | NA |
| 214084_x_at | CD163 | CD163 molecule | acute-phase response, inflammatory response |
| 215049_x_at | AIF1 | allograft inflammatory factor 1 | response to stress, inflammatory response, cell cycle arrest, negative regulation of cell proliferation |
| 215051_x_at | ADA | adenosine deaminase | response to hypoxia, adenosine catabolic process, T cell activation |
| 216705_s_at | FCGR1A, FCGR1C | Fc fragment of IgG, high affinity Ia, Ic, receptor (CD64) | phagocytosis, engulfment |
| 216950_s_at | GLUL | glutamate-ammonia ligase (glutamine synthetase) | glutamine biosynthetic process, nitrogen compound metabolic process |
| 217202_s_at | SNX10 | sorting nexin 10 | transport, cell communication |
| 218404_at | MAFB | v-maf musculoaponeurotic fibrosarcoma oncogene homolog B (avian) | transcription |
| 218559_s_at | CCDC109B | coiled-coil domain containing 109B | NA |
| 218802_at | BIN2 | bridging integrator 2 | NA |
| 219191_s_at | DOCK10 | dedicator of cytokinesis 10 | NA |
| 219279_at | SLAMF8 | SLAM family member 8 | NA |
| 219386_s_at | SIGLEC1 | sialic acid binding Ig-like lectin 1, sialoadhesin | inflammatory response, cell adhesion, cell-matrix adhesion, cell-cell adhesion |
| 219519_s_at | 1-Mar | membrane-associated ring finger (C3HC4) 1 | NA |
| 219574_at | MS4A4A | membrane-spanning 4-domains, subfamily A, member 4 | signal transduction |
| 219607_s_at | MS4A6A | | |
| 219666_at | GAL3ST4 | galactose-3-O-sulfotransferase 4 | sulfur metabolic process, cell-cell signaling, biosynthetic process |
| 219815_at | PSTPIP2 | proline-serine-threonine phosphatase interacting protein 2 | NA |
| 219938_s_at | TLR7 | toll-like receptor 7 | inflammatory response, positive regulation of interferon-gamma biosynthetic process, positive regulation of interleukin-8 biosynthetic process, defense response to virus |
| 220146_at | COTL1 | coactosin-like 1 (*Dictyostelium*) | carbohydrate metabolic process |
| 221059_s_at | NPL | N-acetylneuraminate pyruvate lyase (dihydrodipicolinate synthase) | carbohydrate metabolic process |
| 221210_s_at | SH3BGRL3 | SH3 domain binding glutamic acid-rich protein like 3 | NA |
| 221269_s_at | PYCARD | PYD and CARD domain containing | proteolysis, apoptosis, tumor necrosis factor-mediated signaling pathway, positive regulation of interleukin-1 beta secretion |
| 221666_s_at | CLEC7A | C-type lectin domain family 7, member A | phagocytosis, recognition, inflammatory response, T cell activation, defense response to protozoan |
| 221698_s_at | OBFC2A | oligonucleotide/oligosaccharide-binding fold containing 2A | NA |
| 222872_x_at | CENTA2 | centaurin, alpha 2 | heart development |
| 222876_s_at | MS4A7 | membrane-spanning 4-domains, subfamily A, member 7 | signal transduction |
| 223343_at | | | |
| 223344_s_at | MS4A6A | membrane-spanning 4-domains, subfamily A, member 6A | signal transduction |
| 223922_x_at | | | |
| 224356_x_at | MS4A4A | membrane-spanning 4-domains, subfamily A, member 4 | signal transduction |
| 224357_s_at | COTL1 | coactosin-like 1 (*Dictyostelium*) | NA |
| 224583_at | BCAT1 | branched chain aminotransferase 1, cytosolic | G1/S transition of mitotic cell cycle, metabolic process, cell proliferation, amino acid biosynthetic process |
| 225285_at | C1QC | complement component 1, q subcomponent, C chain | phosphate transport, complement activation, classical pathway |
| 225353_s_at | CTSC | cathepsin C | proteolysis, immune response |
| 225646_at | CTSC | | |
| 225647_s_at | BCAT1 | branched chain aminotransferase 1, cytosolic | G1/S transition of mitotic cell cycle, metabolic process, cell proliferation, amino acid biosynthetic process |

TABLE 1-continued

Overexpressed genes in patients with myocarditis vs idiopathic dilated cardiomyopathy (q < 5%, FC > 2) and their biological function

| Probe Set ID | Gene Symbol | Gene Title | GO biological process term |
| --- | --- | --- | --- |
| 226517_at 226818_at | MPEG1 | macrophage expressed gene 1 | NA |
| 226841_at | FYB | FYN binding protein (FYB-120/130) | carbohydrate metabolic process, protein amino acid phosphorylation, immune response, signal transduction |
| 227266_s_at | RILPL2 | Rab interacting lysosomal protein-like 2 | NA |
| 227983_at | OSR1 | odd-skipped related 1 (*Drosophila*) | heart development |
| 228399_at | C1orf162 | chromosome 1 open reading frame 162 | NA |
| 228532_at | LILRB1 | Leukocyte immunoglobulin-like receptor, subfamily B (with TM and ITIM domains), member 1 | immune response, response to virus |
| 230741_at | MRO | maestro | NA |
| 231358_at | CTSS | cathepsin S | proteolysis, immune response |
| 232617_at | DOCK8 | dedicator of cytokinesis 8 | NA |
| 232843_s_at | OBFC2A | oligonucleotide/oligosaccharide-binding fold containing 2A | NA |
| 233085_s_at | PARVG | parvin, gamma | cell adhesion, cell-matrix adhesion |
| 234987_at | CPM | carboxypeptidase M | proteolysis, anatomical structure morphogenesis |
| 235019_at | HAVCR2 | hepatitis A virus cellular receptor 2 | NA |
| 235458_at | CCL18 | chemokine (C-C motif) ligand 18 (pulmonary and activation-regulated) | chemotaxis, inflammatory response |
| 32128_at | CD52 | CD52 molecule | elevation of cytosolic calcium ion concentration, respiratory burst |
| 34210_at | MAFF | v-maf musculoaponeurotic fibrosarcoma oncogene homolog F (avian) | response to stress, regulation of transcription |
| 36711_at | SIGLEC1 | sialic acid binding Ig-like lectin 1, sialoadhesin | inflammatory response, cell adhesion, cell-matrix adhesion |

TABLE 2

Downregulated genes in patients with myocarditis vs idiopathic dilated cardiomyopathy (q < 5%, FC > 2) and their biological function

| Probe Set ID | Gene Symbol | Gene Title | GO biological process term |
| --- | --- | --- | --- |
| 1552411_at | DEFB106A/B | defensin, beta 106A | defence response, defense response to bacterium |
| 1556721_at | FLJ33706 | hypothetical protein FLJ33706 | NA |
| 1559224_at | LCE1E | late cornified envelope 1E | keratinization |
| 1562256_at 1562257_x_at | NLRP1 | NLR, family pyrin domain containing 1 | induction of apoptosic, caspase activation, defense response |
| 1562785_at | HERC6 | Hect domain and RLD 6 | protein modification process |
| 1564281_at | LOC285708 | hypothetical protein LOC285708 | nucleotide and nucleic acid metabolic process, nervous system development |
| 1564362_x_at | ZNF843 | zinc finger protein 843 | NA |
| 1569568_at | NA | NA | NA |
| 1569569_x_at | NA | NA | NA |
| 213609_s_at | SEZ6L | seizure related 6 homolog (mouse)-like | NA |
| 213791_at | PENK | proenkephalin | behavioral fear response, signal transduction, neuropeptide signaling pathway, sensory perception of pain |
| 224209_s_at | GDA | guanine deaminase | nucleotide and nucleic acid metabolic process, nervous system development |
| 231628_s_at | NA | NA | NA |
| 243909_x_at | GUSBL2 | glucuronidase, beta-like 2 | NA |
| 244891_x_at | NA | NA | NA |

TABLE 3

Overexpressed pathways in patients with myocarditis vs idiopathic dilated cardiomyopathy

| Network | GO Processes | Total nodes | Root nodes | p-Value | zScore |
|---|---|---|---|---|---|
| MafB, MafF, MHC class II, CD44, BCAT1 (Homo sapiens) | system development (66.0%; 2.241e−13); response to stimulus (74.5%; 1.751e−12), multicellular organismal development (68.1%; 7.914e−12), organ development (55.3%; 2.289e−11), positive regulation of cellular process (51.1%; 9.353e−11) | 50 | 10 | 2.43E−17 | 29.34 |
| CCR2, BCAT1, ADA, Annexin II, Pleckstrin (Homo sapiens) | response to external stimulus (53.8%; 2.384e−09), intracellular signaling cascade (57.7%; 1.087e−08), behavior (38.5%; 4.275e−08), response to chemical stimulus (53.8%; 8.258e−08), MAPKKK cascade (26.9%; 1.123e−07) | 50 | 7 | 1.97E−12 | 24.29 |
| p47-phox, CCR2, p67-phox, Pleckstrin, IL-12 receptor (Homo sapiens) | protein kinase cascade (48.8%; 2.208e−20), intracellular signaling cascade (68.3%; 6.669e−18); response to chemical stimulus (61.0%; 1.232e−14), regulation or cell migration (29.3%; 3.332e−14), MAPKEK cascade (31.7%; 3.194e−14) | 50 | 7 | 1.53E−11 | 21.11 |
| C1q, CD44, CD14, SLAP-130(ADAP), alpha-4/beta-1 integrin (Homo sapiens) | cell-matrix adhesion (30.4%; 2.499e−10) cell-substrate adhesion (30.4%; 4.574e−10), positive regulation of biological process (69.6%; 1.047e−09), cell adhesion (47.8%; 2.037e−03), biological adhesion (47.8%; 2.037e−08) | 24 | 4 | 2.85E−07 | 16.72 |
| Plastin, IRT-1 (Homo sapiens) | actin filament bundle formation (100.0%; 1.902e−05), actin filament organization (100.0%; 5.224e−05), actin cytoskeleton organization (100.0%; 4.702e−04), actin filament-based process (100.0%; 5.330e−04), macrophage activation (50.0%; 2.438e−03) | 2 | 2 | 5.36E−06 | 29.3 |
| CD163, HP/HB complex (Homo sapiens) | acute inflammatory response (100.0%; 1.664e−04), response to L-ascorbic acid (50.0%; 4.879e−04), nitric oxide transport (50.0%; 4.879e−04), inflammatory response (100.0%; 1.161e−03), response to magnesium ion (50.0%; 1.341e−03) | 2 | 1 | 4.64E−03 | 14.62 |
| Complement component C1, Complement C4 = Complement component C4a + Complement component C4b, Complement C2 = Complement component C2a + Complement component C2b, Complement component C4a, C4a (Homo sapiens) | complement activation, classical pathway (100.0%; 3.660e−03), glial cell differentiation (100.0%; 3.904e−03), humoral immune response mediated by circulating immunoglobulin (100.0%; 4.026e−03); activation of plasma proteins during acute inflammatory response (100.0%; 4.819e−03), complement activation (100.0%; 4.819e−03) | 8 | 1 | 1.16E−02 | 9.18 |
| PLTP, ABCA1, CREB1, Cholesterol extracellular region, Cholesterol + ATP + H($_2$)O = Cholesterol + ADP + PO($_4$)('3−) (Homo sapiens) | response to drug (60.0%; 7.494e−05), platelet dense granule organization and biogenesis (20.0%; 3.050e−04), response to vitamin K (20.0%; 3.050e−04), response to menaquinane (20.0%; 3.050e−04), positive regulation of growth (40.0%; 3.354e−04) | 19 | 1 | 3.88E−02 | 4.84 |

TABLE 4

Molecular signature that discriminates giant cell myocarditis from idiopathic dilated cardiomyopathy

| Probe Set ID | Gene Symbol | Gene Title | Go Biological Process Term |
|---|---|---|---|
| 210067_at | AQP4 | aquaporin 4 | Transport, water transport, nervous system development, excretion |
| 221212_x_at | PBRM1 | polybromo 1 | chromatin remodeling, regulation of transcription, mitosis, chromatin modification |
| 227145_at | LOXL4 | lysyl oxidase-like-4 | oxidation reduction |
| 228329_at | DAB1 | disabled homolog 1 (Drosophila) | multicellular organismal development, nervous system development, cell differentiation |
| 231577_s_at | GBP1 | guanylate binding protein 1, interferon-inducible, 67 kDa | immune response |
| 231906_at | HOXD8 | Homeobox D8 | regulation of transcription, multicellular organismal development, determination of anterior/posterior axis, embryo, regulation of transcription |

TABLE 4-continued

Molecular signature that discriminates giant cell myocarditis from idiopathic dilated cardiomyopathy

| Probe Set ID | Gene Symbol | Gene Title | Go Biological Process Term |
|---|---|---|---|
| 235334_at | ST6GALNAC3 | ST6 (alpha-N-acetyl-neuraminyl-2,3-beta-galactosyl-1,3)-N-acetylgalactosaminide alpha-2,6-sialyltransferase 3 | protein amino acid glycosylation |
| 237783_at | PLAC8L1 | PLAC8-like-1 | NA |

TABLE 5

Molecular signature that discriminates sarcoidosis from idiopathic dilated cardiomyopathy

| Probe Set ID | Gene Symbol | Gene Title | Go Biological Process Term |
|---|---|---|---|
| 1552974_at | NA | NA | NA |
| 1553781_at | ZC3HAV1L | zinc finger CCCH-type, antiviral 1-like | NA |
| 1554478_a_at | HEATR3 | HEAT repeat containing 3 | NA |
| 1556760_a_at | NA | NA | NA |
| 1556883_a_at | LOC440896 | hypothetical gene LOC440896 | NA |
| 1557717_at | LOC338862 | hypothetical protein LOC338862 | NA |
| 1560144_at | NA | NA | NA |
| 1560683_at | BCL8 | B-cell CLL/lymphoma 8 | NA |
| 1560684_x_at | BCL8 | B-cell CLL/lymphoma 8 | NA |
| 1561543_at | NA | NA | NA |
| 1562035_at | NA | NA | NA |
| 1563054_at | NA | NA | NA |
| 1563452_at | KIAA0241 | KIAA0241 | NA |
| 1564107_at | NA | NA | NA |
| 1564733_at | NA | NA | NA |
| 1565788_at | NA | NA | NA |
| 1566550_at | NA | NA | NA |
| 1568589_at | NA | NA | NA |
| 201291_s_at | TOP2A | topoisomerase (DNA) II alpha 170 kDa | DNA metabolic process, DNA replication, response to DNA damage stimulus, apoptotic chromosome condensation, positive regulation of viral genome replication, positive regulation of retroviral genome replication |
| 204666_s_at | RP5-1000E10.4 | exppressor of IKK epsilon | NA |
| 208536_s_at | BCL2L11 | BCL2-like 11 (apoptosis facilitator) | Induction of apoptosis, activation of pro-apoptotic gene products |
| 209371_s_at | SH3BP2 | SH3-domain binding protein 2 | signal transduction |
| 215512_at | 6-Mar | membrane-associated ring finger (C3HC4) 6 | NA |
| 216947_at | DES | desmin | muscle contraction, cytoskeleton organization and biogenesis, regulation of heart contraction |
| 217292_at | MTMR7 | myotubularin related protein 7 | protein amino acid dephosphorylation, phospholipid dephosphorylation |
| 218554_a_at | ASH1L | ash1 (absent, small, or homeotic)-like (*Drosophila*) | DNA packaging, regulation of transcription, transcription from RNA polymerase II promoter, cell-cell signalling, chromatin modification |
| 218585_s_at | DTL | denticleless homolog (*Drosophila*) | DNA replication, response to DNA damage stimulus |
| 219258_at | TIPIN | TIMELESS interacting protein | DNA replication checkpoint, response to DNA damage stimulus, cell cycle, mitosis, positive regulation of cell proliferation, intra-S DNA damage checkpoint, replication fork protection, cell division |
| 219735_s_at | TFCP2L1 | transcription factor CP2-like 1 | Negative regulation of transcription from RNA polymerase II promoter, cell morphogenesis, epithelial cell maturation, regulation of transcription, steroid biosynthetic process, determination of adult life span |
| 219918_s_at | ASPM | asp (abnormal spindle) homolog, microcephaly associated (*Drosophila*) | cell cycle, mitosis, cell division |
| 220085_at | HELLS | helicase, lymphoid-specific | methylation-dependent chromatin silencing, regulation of transcription, cell cycle, mitosis, multicellular organismal development, centromeric heterochromatin formation, lymphocyte proliferation |
| 220735_s_at | SENP7 | SUMO1/sentrin specific peptidase 7 | Proteolysis, protein sumoylation |
| 220930_s_at | MGC5590 | hypothetical protein MGC5590 | NA |
| 221212_x_at | PBRM1 | polybromo 1 | chromatin remodeling, regulation of transcription, DNA-dependent, mitosis, chromatin modification |
| 221268_s_at | SGPP1 | sphingosine-1-phosphate phosphatase 1 | splingolipid metabolic process, splingamine-1-phosphate metabolic process, apoptosis |

TABLE 5-continued

Molecular signature that discriminates sarcoidosis from idiopathic dilated cardiomyopathy

| Probe Set ID | Gene Symbol | Gene Title | Go Biological Process Term |
| --- | --- | --- | --- |
| 221969_at | NA | NA | NA |
| 223700_at | MND1 | meiotic nuclear divisions 1 homolog (*S. cerevisiae*) | DNA recombination, meiosis |
| 223865_at | SOX6 | SRY (sex determining region Y)-box 6 | establishment or maintenance of chromatin architecture, regulation of transcription, multicellular organismal development, muscle development |
| 224424_x_at | LOC440888 | ARP3 actin-related protein 3 homolog B pseudogene | regulation of actin filament polymerization |
| 224426_s_at | LOC440888 | ARP3 actin-related protein 3 homolog B pseudogene | regulation of actin filament polymerization |
| 232453_at | NA | NA | NA |
| 233786_at | NA | NA | NA |
| 235588_at | ESCO2 | establishment of cohesion 1 homolog 2 (*S. cerevisiae*) | DNA repair, cell cycle |
| 235661_at | NA | NA | NA |
| 235899_at | CA13 | carbonic anhydrase XIII | one-carbon compound metabolic process |
| 236628_at | NA | NA | NA |
| 236740_at | NA | NA | NA |
| 237289_at | CREB1 | cAMP responsive element binding protein 1 | regulation of transcription, protein amino acid phosphorylation, signal transduction, interspecies interaction between organisms |
| 238370_x_at 238375_at | RPL22 | Ribosomal protein L22 | Translation, translational elongation |
| 239486_at | NA | NA | NA |
| 239899_at | RNF145 | Ring finger protein 145 | NA |
| 241922_at | NA | NA | NA |
| 242784_at | NA | NA | NA |
| 242939_at | TFDP1 | transcription factor Dp-1 | S phase of mitotic cell cycle, regulation of transcription, apoptosis, cell proliferation, epidermis development |
| 244356_at | NA | NA | NA |
| 244609_at | NA | NA | NA |
| 37892_at | COL11A1 | collagen type XI, alpha 1 | cartilage condensation, phosphate transport, cell adhesion, extracellular matrix organisation and biogenesis |

TABLE 6

Molecular signature that discriminates peripartum cardiomyopathy from idiopathic dilated cardiomyopathy

| Probe Set ID | Gene Symbol | Gene Title | Go Biological Process Term |
| --- | --- | --- | --- |
| 1553972_a_at | CBS | cystathionine-beta synthase | cysteine metabolic process |
| 1557833_at | NA | NA | NA |
| 1560395_at | NA | NA | NA |
| 201909_at | LOC100133662, RPS4Y1 | hypothetical protein LOC100133662, ribosomal protein S4, Y-linked 1 | translational elongation |
| 204409_s_at 204410_at | EIF1AY | eukaryotic translation initiation factor 1A, Y-linked | translational initiation |
| 205000_at 205001_s_at | DDX3Y | DEAD (Asp-Glu-Als-Asp) box polypeptide 3, Y-linked | NA |
| 205033_s_at | DEFA1, DEFA3, LOC728358 | defensin, alpha 1, defensin, alpha 3, neutrophil-specific defensin, alpha 1 | xenobiotic metabolic process, chemotaxis, defense response, immune response, response to virus, defense response to bacterium, defense response to fungus |
| 205048_s_at | PSPH | phosphoserine phosphatase | L-serine metabolic process |
| 205609_at | ANGPT1 | angiopoietin 1 | Angiogenesis, signal transduction, multicellular organismal development, cell differentiation |
| 206624_at | LOC100130216, USP9Y | hypothetical protein LOC100130216, ubiquitin specific peptidase 9, Y-linked (fat facets-like, *Drosophila*) | ubiquitin-dependent protein carbolic process |
| 206700_s_at | JARID1D | jumonji, AT rich interactive domain 1D | chromatin modification, oxidation reduction |
| 207063_at | CYorf14 | chromosome Y open reading frame 14 | NA |
| 208067_x_at | LOC100130224, UTY | hypothetical protein LOC100130224, ubiquitously transcribed tetratricopeptide repeat gene, Y-linked | chromatin modification, oxidation reduction |

TABLE 6-continued

Molecular signature that discriminates peripartum cardiomyopathy from idiopathic dilated cardiomyopathy

| Probe Set ID | Gene Symbol | Gene Title | Go Biological Process Term |
|---|---|---|---|
| 209771_x_at | CD24 | CD24 molecule | response to hypoxia, cell activation, regulation of cytokine and chemokine mediated signaling pathway, response to molecule of bacterial origin, immune response-regulating cell surface receptor signaling pathway, elevation of cytosolic calcium ion concentration, neuromuscular synaptic transmission, induction of apoptosis by intracellular signals, Wnt receptor signaling pathway, cell-cell adhesion, positive regulation of activated T cell proliferation |
| 211018_at | LSS | lanosterol synthase (2,3-oxidosqualene-lanosterol cyclase) | steroid biosynthetic process, metabolic process, steroid metabolic process, lipid biosynthetic process |
| 211149_at | LOC100130224, UTY | hypothetical protein LOC100130224, ubiquitously transcribed tetratricopeptide repeat gene, Y-linked | chromatin modification, oxidation reduction |
| 212768_s_at | OLFM4 | olfactomedin 4 | cell adhesion |
| 212816_s_at | CBS | cystathionine-beta-synthase | cysteine metabolic process |
| 212906_at | GRAMD1B | GRAM domain containing 1B | NA |
| 214131_at | CYorf15B | chromosome Y open reading frame 15B | NA |
| 214218_s_at | XIST | X (inactive)-specific transcript (non-protein coding) | NA |
| 214983_at | TTTY15 | testis-specific transcript, Y-linked 15 | NA |
| 216758_at | NA | NA | NA |
| 219938_s_at | PSTPIP2 | proline-serine-threonine phosphatase interacting protein 2 | NA |
| 221728_x_at | XIST | X (inactive)-specific transcript (non-protein coding) | NA |
| 223645_s_at 223646_s_at | CYorf15B | chromosome Y open reading frame 15B | NA |
| 224293_at | TTTY10 | testis-specific transcript, Y-linked 10 | NA |
| 224588_at 224589_at 224590_at 227671_at | XIST | X (inactive)-specific transcript (non-protein coding) | NA |
| 227742_at | CLIC6 | chloride intracellular channel 6 | Transport, ion transport, chloride transport |
| 228194_s_at | SORCS1 | sortilin-related VPS10 domain containing receptor 1 | neuropeptide signaling pathway |
| 228492_at | LOC100130216, USP9Y | hypothetical protein LOC100130216, ubiquitin specific peptidase 9, Y-linked (fat facets-like, Drosophila) | ubiquitin-dependent protein catabolic process |
| 229160_at | MUM1L1 | melanoma associated antigen (mutated) 1-like 1 | NA |
| 229534_at | ACOT4 | acyl-CoA thioesterase 4 | very-long-chain fatty acid metabolic process, long-chain fatty acid metabolic process, succinyl-CoA metabolic process, lipid metabolic process, acyl-CoA metabolic process, saturated monocarboxylic acid metabolic process, unsaturated monocarboxylic acid metabolic process, dicarboxylic acid metabolic process, short-chain fatty acid metabolic process |
| 239104_s_at | TPPP | tubulin polymerization promoting protein | microtubule bundle formation, positive regulation of protein complex assembly, microtubule polymerization |
| 230760_at | LOC100130829, ZFY | hypothetical protein LOC100130829, zinc finger protein, Y-linked | regulation of transcription |
| 231592_at | TSIX | X (inactive)-specific transcript, antisense (non-protein coding) | NA |
| 232365_at | SIAH1 | seven in absentia homolog 1 (Drosophila) | Proteolysis, ubiquitin-dependent protein carabolic process, apoptosis, cell cycle, multicellular organismal development, nervous system development, axon guidance, cell differentiation |
| 232618_at | CYorf15A | chromosome Y open reading frame 15A | NA |
| 233176_at | NA | NA | NA |
| 235334_at | ST6GALNAC3 | ST6 (alpha-N-acetyl-neuraminyl-2,3-beta-galactosyl-1,3)-N-acetylgalactosaminide alpha-2,6-sialyltransferase 3 | protein amino acid glycosylation |
| 235446_at | NA | NA | NA |
| 235942_at | LOC401629, LOC401630 | LOC401629, LOC401630 | NA |

TABLE 6-continued

Molecular signature that discriminates peripartum cardiomyopathy from idiopathic dilated cardiomyopathy

| Probe Set ID | Gene Symbol | Gene Title | Go Biological Process Term |
|---|---|---|---|
| 236694_at | CYorf15A | chromosome Y open reading frame 15A | NA |
| 239568_at | PLEKHH2 | pleckstrin homology domain containing, family H (with MyTH4 domain) member 2 | NA |
| 239584_at | NA | NA | NA |
| 239677_at | NA | NA | NA |
| 242316_at | NA | NA | NA |
| 243610_at | C9orf135 | chromosome 9 open reading frame 135 | NA |
| 244482_at | NA | NA | NA |
| 266_s_at | CD24 | CD24 molecule | response to hypoxis, cell activation, regulation of cytokine and chemokine mediated signaling pathway, response to molecule of bacterial origin, immune response-regulating cell surface receptor signaling pathway, elevation of cytosolic calcium ion concentration, neuromuscular synaptic transmission, induction of apoptosis by intracellular signals, Wnt receptor signaling pathway, cell-cell adhesion, positive regulation of activated T cell proliferation |

TABLE 7

Molecular signature that discriminates systemic lupus erythematosus from idiopathic dilated cardiomyopathy

| Probe Set ID | Gene Symbol | Gene Title | Go Biological Process Term |
|---|---|---|---|
| 1552946_at | ZNF114 | zinc finger protein 114 | Regulation of transcription |
| 1553607_at | C21orf109 | chromosome 21 open reading frame 109 | NA |
| 1555485_s_at | FAM153B | family with sequence similarity 153, member B | NA |
| 1558882_at | LOC401233 | cofactor required for Tat activation of HIV-1 transcription | NA |
| 1561012_at | NA | NA | NA |
| 1566518_st | NA | NA | NA |
| 1569539_at | NA | NA | NA |
| 1569794_st | NA | NA | NA |
| 207781_s_at | ZNF711 | zinc finger protein 711 | Regulation of transcription |
| 222375_at | NA | NA | NA |
| 229288_at | NA | NA | NA |
| 229523_at | TTMA | Two transmembrane domain family member A | NA |
| 235803_at | NA | NA | NA |
| 238533_at | EPHA7 | EPH receptor A7 | protein amino acid phosphorylation, transmembrane receptor protein tyrosine kinase signaling pathway |
| 238755_at | NA | NA | NA |
| 240783_at | NA | NA | NA |
| 240903_at | NA | NA | NA |
| 242641_at | NA | NA | NA |
| 243012_at | NA | NA | NA |
| 244626_at | NA | NA | NA |
| 244636_at | NA | NA | NA |

TABLE 8

Molecular signature that differentiates giant cell myocarditis from lymphocytic myocarditis

| Probe Set ID | Gene Symbol | Gene Title | Go Biological Process Term |
|---|---|---|---|
| 1563283_at | NA | NA | NA |
| 204477_at | RABIF | RAB interacting factor | Transpost, membrane fusion, small GTPase mediated signal transduction, protein transport |
| 205275_at | GTPBP1 | GTP binding protein 1 | immune response, signal transduction, cell redox homeostasis |
| 214313_s_at | EIF5B | Eukaryotic translation initiation factor 5B | regulation of translational initiation |

TABLE 9

Molecular signature that differentiates sarcoidosis from lymphocytic myocarditis

| Probe Set ID | Gene Symbol | Gene Title | go biological process term |
|---|---|---|---|
| 204477_at | RABIF | RAB interacting factor | Transport, membrane fusion, small GTPase mediated signal transduction, protein transport |
| 205275_at | GTPBP1 | GTP binding protein 1 | immune response, signal transduction, cell redox homeostasis |
| 214313_s_at | EIF5B | Eukaryotic translation initiation factor 5B | Translation, regulation of translational initiation |
| 224500_s_at | MON1A | MON1 homolog A (yeast) | NA |
| 236093_at | NA | NA | NA |
| 243564_at | PDE1C | phosphodiesterase 1C, calmodulin-dependent 70 kDa | signal transduction |

15

TABLE 10

Molecular signature that differentiates peripartum cardiomyopathy from lymphocytic myocarditis

| Probe Set ID | Gene Symbol | Gene Title | Go Biological Process Term |
|---|---|---|---|
| 1563283_at | NA | NA | NA |
| 205275_at | GTPBP1 | GTP binding protein 1 | immune response, signal transduction, cell redox homeostasis |
| 207300_s_at | F7 | coagulation factor VII (serum prothrombin conversion accelerator) | Proteolysis, blood coagulation, extrinsic pathway |
| 214313_s_at | EIF5B | Eukaryotic translation initiation factor 5B | regulation of translational initiation |
| 214473_x_at | PMS2L3 | postmeiotic segregation increased 2-like 3 | mismatch repair, regulation of transcription |
| 227509_x_at | NA | NA | NA |
| 228232_s_at | VSIG2 | V-set and immunoglobulin domain containing 2 | NA |
| 230731_x_at | ZDHHC8 | zinc finger, DHHC-type containing 8 | NA |
| 232586_x_at | LOC100133315 | Similar to hCG1640299 | single strand break repair |
| 236093_at | NA | NA | NA |
| 237867_s_at | PID1 | phosphotyrosine interaction domain containing 1 | NA |
| 243564_at | PDE1C | phosphodiesterase 1C, calmodulin-dependent 70 kDa | signal transduction |

TABLE 11

Molecular signature that differentiates systemic lupus erythematosus from lymphocytic myocarditis

| Probe Set ID | Gene Symbol | Gene Title | Go Biological Process Term |
|---|---|---|---|
| 1556205_at | NA | NA | NA |
| 202179_at | BLMH | bleomycin hydrolase | Proteolysis, response to toxin, response to drug |
| 203134_at | PICALM | phosphatidylinositol binding clathrin assembly protein | protein complex assembly, endocytosis, receptor-mediated endocytosis, receptor-mediated endocytosis, vesicle-mediated transport, clathrin coat assembly |
| 203540_at | GFAP | glial fibrillary acidic protein | NA |
| 205554_s_at | DNASE1L3 | deoxyribonuclease I-like 3 | DNA metabolic process, DNA catabolic process, DNA fragmentation during apoptosis |
| 205673_s_at | ASB9 | ankyrin repeat and SOCS box-containing 9 | intracellular signaling cascade |
| 205794_s_at | NOVA1 | neuro-oncological ventral antigen 1 | RNA processing, synaptic transmission, locomotory behavior, RNA splicing |
| 209220_at | GPC3 | glypican 3 | anatomical structure morphogenesis |
| 209304_s_at | GADD45B | growth arrest and DNA-damage-inducible, beta | activation of MAPKKK activity, negative regulation of protein kinase activity, apoptosis, response to stress, multicellular organismal development cell differentiation |
| 209540_at | IGF1 | insulin-like growth factor 1 (somatomedin C) | skeletal development, DNA replication, anti-apoptosis, muscle development, positive regulation of cell proliferation, satellite cell maintenance involved in skeletal muscle regeneration, muscle hypertrophy, myotube cell development positive regulation of tyrosine phosphorylation of Stat5 protein, myoblast differentiation, positive regulation of fibroblast proliferation |
| 209923_s_at | BRAP | BRCA1 associated protein | negative regulation of signal transduction |

TABLE 11-continued

Molecular signature that differentiates systemic lupus erythematosus from lymphocytic myocarditis

| Probe Set ID | Gene Symbol | Gene Title | Go Biological Process Term |
| --- | --- | --- | --- |
| 212173_at | AK2 | adenylate kinase 2 | nucleobase, nucleoside, nucleotide and nucleic acid metabolic process |
| 213496_at | LPPR4 | plasticity related gene 1 | NA |
| 214358_at | DNAJB12 | DnaJ (Hsp40) homolog, subfamily B, member 12 | protein folding |
| 216269_s_at | ELN | elastin | DNA repair, respiratory geneous exchange, blood circulation, cell proliferation organ morphogenesis |
| 217950_at | NOSIP | nitric oxide synthase interacting protein | protein ubiquitination, negative regulation of catalytic activity, negative regulation of nitric-oxide synthase activity |
| 218180_s_at | EPS8L2 | EPS8-like 2 | NA |
| 220117_at | ZNF385D | zinc finger protein 385D | NA |
| 220941_s_at | C21orf91 | chromosome 21 open reading frame 91 | NA |
| 222002_at | C7orf26 | Chromosome 7 open reading frame 26 | NA |
| 222879_s_at | POLH | polymerase (DNA directed), eta | DNA synthesis during DNA repair |
| 223574_x_at | PPP2R2C | protein phosphatase 2 (formerly 2A), regulatory subunit B, gamma isoform | signal transduction |
| 223586_at | ARNTL2 | aryl hydrocarbon receptor nuclear translocator-like 2 | regulation of transcription, signal transduction, entrainment of circadian clock |
| 230974_at | DDX19B | DEAD (Asp-Glu-Ala-As) box polypeptide 19B | mRNA export from nucleus, intracellular protein transport across a membrane |
| 233298_at | C13orf38 SOHLH2 | chromosome 13 open reading frame 38, spermatogenesis and oogenesis specific basic helix-loop-helix 2 | regulation of transcription, multicellular organismal development, cell differentiation |
| 238151_at | NA | NA | NA |
| 243076_x_at | GLI4 | GLI-Kruppel family member GLI4 | NA |

TABLE 12

Molecular signature to distinguish giant cell myocarditis from sarcoidosis

| Probe Set ID | Gene Symbol | Gene Title | Go Biological Process Term |
| --- | --- | --- | --- |
| 1553894_at | CCDC122 | coiled-coil domain containing 122 | NA |
| 1557311_at | LOC100131354 | Hypothetical protein LOC100131354 | NA |
| 1557996_at | POLR2J4 | polymerase (RNA) II (DNA directed) polypeptide J4, pseudogene | transcription |
| 1558450_at | NA | NA | NA |
| 1559227_s_at | VHL | von Hippel-Lindau tumor suppressor | negative regulation of transcription from RNA polymerase II promoter, cell morphogenesis, proteolysis, anti-apoptosis, response to stress, negative regulation of cell proliferation, regulation of cell differentiation, negative regulation of cell cycle |
| 1561789_at | NA | NA | NA |
| 1569312_at | NA | NA | NA |
| 205238_at | CXorf34 | chromosome X open reading frame 34 | NA |
| 211734_s_at | FCER1A | Fc fragment of IgE, high affinity I, receptor for, alpha polypeptide | positive regulation of type I hypersensitivity, serotonin secretion, cell surface receptor linked signal transduction, leukotriene biosynthetic process, positive regulation of mast cell degranulation, positive regulation of interleukin-3 biosynthetic process, positive regulation of granulocyte macrophage colony-stimulating factor biosynthetic process |
| 218669_at | RAP2C | RAP2C, member of RAS oncogene family | small GTPase mediated signal transduction |
| 225207_at | PDK4 | pyruvate dehydrogenase kinase, isozyme 4 | carbohydrate metabolic process, glucose metabolic process, signal transduction, phosphorylation |
| 231114_at | SPATA22 | spermatogenesis associated 22 | NA |
| 231418_at | NA | NA | NA |
| 231819_at | NA | NA | NA |
| 231956_at | KIAA1618 | KIAA1618 | NA |

TABLE 12-continued

Molecular signature to distinguish giant cell myocarditis from sarcoidosis

| Probe Set ID | Gene Symbol | Gene Title | Go Biological Process Term |
|---|---|---|---|
| 233927_at | NA | NA | NA |
| 239151_at | CTGLF6 | centaurin, gamma-like family, member 6 | regulation of ARF GTPase activity |
| 241788_x_at | NA | NA | NA |
| 242691_at | NA | NA | NA |

TABLE 13

Baseline conditions of patients with idiopathic dilated cardiomyopathy and lymphocytic myocarditis

| | Idiopathic dilated cardiomyopathy (n = 32) | Myocarditis (n = 16) |
|---|---|---|
| Age | 48 (±3) | 45 (±6) |
| Male, n (%) | 11 (38) | 11 (69) |
| NYHA, n (%) | | |
| I | 9 (28) | 4 (25) |
| II | 10 (31) | 3 (19) |
| III | 13 (59) | 8 (50) |
| IV | 3 (9) | 1 (6) |
| LV EF, % | 26 ± 2 | 33 ± 4 |
| LVIDD, cm | 5 ± 0.3 | 5 ± 0.2 |
| PAP, mmHg | | |
| Systolic | 38 ± 3 | 37 ± 3 |
| Diastolic | 18 ± 2 | 15 ± 2 |
| PCWP, mmHg | 15 ± 2 | 12 ± 2 |
| Systolic BP, mmHg | 128 ± 5 | 119 ± 5 |
| Diastolic BP, mmHg | 76 ± 2 | 70 ± 4 |
| Medications, n (%) | | |
| B-Antagonist | 20 (62) | 9 (56) |
| ACE inhibitor | 20 (62) | 14 (88) |
| Aldosterone antagonist | 4 (13) | 1 (6) |
| Diuretic | 14 (64) | 13 (81) |
| Intravenous inotropic therapy | NA | NA |

Statistics: Student t-test, Fisher Exact test; ± refers to standard error of the mean

TABLE 14

Transcriptomic diagnostic biomarker for detection of patients with myocarditis: 62 genes

| Probe Set ID | Gene Symbol | Gene Title | GO biological process term |
|---|---|---|---|
| 1552302_at | FLJ77644, TMEM106A | similar to transmembrane protein 106A, transmembrane protein 106A | NA |
| 1552310_at | C15orf40 | chromosome 15 open reading frame 40 | NA |
| 1553212_at | KRT78 | keratin 78 | NA |
| 1555349_s_at | ITGB2 | integrin, beta 2 (complement component 3 receptor 3 and 4 subunit) | apoptosis, inflammatory response, leukocyte adhesion |
| 1555878_at | RPS24 | Ribosomal protein S24 | translation |
| 1556033_at | NA | NA | NA |
| 1556507_at | NA | NA | NA |
| 1558605_at | NA | NA | NA |
| 1559224_at | LCE1E | late cornified envelope 1E | keratinization |
| 1562785_at | HERC6 | Hect domain and RLD 6 | protein modification process |
| 1565662_at | NA | NA | maintenance of gastrointestinal epithelium |
| 1565830_at | NA | NA | NA |
| 202375_at | SEC24D | SEC24 related gene family, member D (*S. cerevisiae*) | transport, intracellular protein transport |
| 202445_s_at | NOTCH2 | Notch homolog 2 (*Drosophila*) | cell fate determination |
| 203741_s_at | ADCY7 | adenylate cyclase 7 | cAMP biosynthetic process, signal transduction |
| 204222_s_at | GLIPR1 | GLI pathogenesis-related 1 | NA |
| 206052_s_at | SLBP | stem-loop binding protein | mRNA processing, histone mRNA 3'-end processing |
| 206333_at | MSI1 | musashi homolog 1 (*Drosophila*) | nervous system development |
| 206770_s_at | SLC35A3 | solute carrier family 35 (UDP-N-acetylglucosamine (UDP-GlcNAc) transporter), member A3 | UDP-N-acetylglucosamine metabolic process, transport, |
| 209307_at | SWAP70 | SWAP-70 protein | somatic cell DNA recombination, isotype switching |
| 211089_s_at | NEK3 | NIMA (never in mitosis gene a)-related kinase 3 | protein amino acid phosphorylation. mitosis |
| 211341_at | LOC100131317, POU4F1 | similar to hCG1781072, POU class 4 homeobox 1 | transcription, regulation of transcription, DNA-dependent, regulation of transcription from RNA polymerase II promoter |
| 212511_at | PICALM | phosphatidylinositol binding clathrin assembly protein | protein complex assembly, endocytosis, receptor-mediated endocytosis |

TABLE 14-continued

Transcriptomic diagnostic biomarker for detection of patients with myocarditis: 62 genes

| Probe Set ID | Gene Symbol | Gene Title | GO biological process term |
| --- | --- | --- | --- |
| 212830_at | MEGF9 | multiple EGF-like-domains 9 | NA |
| 212999_x_at | hCG_1998957, HLA-DQB1/2, HLA-DRB1/2/3/4/5 | major histocompatibility complex, class II, DR beta 1/2/3/4/5; similar to major histocompatibility complex, class II, DQ beta 1 | antigen processing and presentation of peptide or polysaccharide antigen via MHC class II |
| 213501_at | ACOX1 | acyl-Coenzyme A oxidase 1, palmitoyl | generation of precursor metabolites and energy, lipid metabolic process |
| 213831_at | HLA-DQA1 | major histocompatibility complex, class II, DQ alpha 1 | antigen processing and presentation of peptide or polysaccharide antigen via MHC class II |
| 217054_at | NA | NA | NA |
| 217182_at | MUC5AC | mucin 5AC, oligomeric mucus/gel-forming | cell adhesion, digestion, fibril organization and biogenesis |
| 217322_x_at | NA | NA | NA |
| 217777_s_at | PTPLAD1 | protein tyrosine phosphatase-like A domain containing 1 | I-kappaB kinase/NF-kappaB cascade |
| 218803_at | CHFR | checkpoint with forkhead and ring finger domains | protein polyubiquitination, mitotic cell cycle, ubiquitin-dependent protein catabolic process |
| 219425_at | SULT4A1 | sulfotransferase family 4A, member 1 | lipid metabolic process, steroid metabolic process |
| 221663_x_at | HRH3 | histamine receptor H3 | signal transduction, G-protein coupled receptor protein signaling pathway, neurotransmitter secretion |
| 223077_at | TMOD3 | tropomodulin 3 (ubiquitous) | NA |
| 224327_s_at | DGAT2 | diacylglycerol O-acyltransferase homolog 2 (mouse) | glycerol metabolic process, lipid metabolic process, lipid biosynthetic process, triacylglycerol biosynthetic process |
| 224996_at | NA | NA | NA |
| 225579_at | PQLC3 | PQ loop repeat containing 3 | NA |
| 226240_at | MGC21874 | transcriptional adaptor 2 (ADA2 homolog, yeast)-beta | transcription, regulation of transcription, DNA-dependent |
| 227280_s_at | CCNYL1 | Cyclin Y-like 1 | NA |
| 227618_at | NA | NA | NA |
| 227983_at | RILPL2 | Rab interacting lysosomal protein-like 2 | NA |
| 228980_at | RFFL | ring finger and FYVE-like domain containing 1 | intracellular protein transport, apoptosis |
| 229191_at | TBCD | tubulin folding cofactor D | protein folding, beta-tubulin folding |
| 230836_at | ST8SIA4 | ST8 alpha-N-acetyl-neuraminide alpha-2,8-sialyltransferase 4 | protein modification process, protein amino acid glycosylation, nervous system development |
| 231599_x_at | DPF1 | D4, zinc and double PHD fingers family 1 | transcription, regulation of transcription, DNA-dependent, induction of apoptosis |
| 234495_at | KLK15 | kallikrein-related peptidase 15 | proteolysis |
| 234986_at | NA | NA | NA |
| 234987_at | NA | NA | NA |
| 236232_at | STX4 | Syntaxin 4 | transport, neurotransmitter transport, intracellular protein transport |
| 236404_at | NA | NA | NA |
| 236698_at | NA | NA | NA |
| 238327_at | LOC440836 | similar to MGC52879 protein | cell growth |
| 238445_x_at | MGAT5B | mannosyl (alpha-1,6-)-glycoprotein beta-1,6-N-acetyl-glucosaminyltransferase, isozyme B | NA |
| 239463_at | NA | NA | NA |
| 242383_at | NA | NA | NA |
| 242563_at | NA | NA | NA |
| 243819_at | NA | NA | NA |
| 244841_at | SEC24A | SEC24 related gene family, member A (S. cerevisiae) | transport, intracellular protein transport, ER to Golgi vesicle-mediated transport |
| 32069_at | N4BP1 | NEDD4 binding protein 1 | NA |
| 44673_at | SIGLEC1 | sialic acid binding Ig-like lectin 1, sialoadhesin | inflammatory response, cell adhesion |
| 53720_at | C19orf66 | chromosome 19 open reading frame 66 | NA |

TABLE 15

Most predictive gene signatures identified by MiPP in a dataset of patients with myocarditis (n = 16) vs idiopathic dilated cardiomyopathy in training (n = 32): Validation was performed in independent test sets (n = 18).

| Gene signatures | Selection method | Prediction rule | Class comparison | Mean ER in training set | Mean ER in validation set |
|---|---|---|---|---|---|
| MSI1, 1556507_at | MiPP | SVM-rbf | 2 | 0 | 0.167 |
| KRT78 | MiPP | SVM-lin | 2 | 0.033 | 0.167 |
| KRT78, 1556507_at | MiPP | QDA | 2 | 0 | 0.167 |
| KRT78, 1556507_at | MiPP | LDA | 2 | 0 | 0.167 |
| 1556507_at | MiPP | LDA, QDA, SVM-rbf | 2 | 0 | 0.167 |

TABLE 16

Models obtained from 50 random splits into train and test set: Genes obtained from 50 random splits were further validated in 200 independent random splits. Illustrated are the results from the top 5 gene clusters with the lowest mean error (ER). Mean sMipp is an additional parameter for performance and converges towards 1, as accuracy of the model increases.

| Split | Gene1 | Gene2 | Gene3 | Gene4 | Gene5 | Gene6 | mean ER | mean sMiPP | 5% ER | 50% ER | 95% ER |
|---|---|---|---|---|---|---|---|---|---|---|---|
| 17 | KRT78 | 1556507_at | NA | NA | NA | NA | 0.078 | 0.789 | 0.188 | 0.063 | 0 |
| 45 | KRT78 | 1556507_at | NA | NA | NA | NA | 0.078 | 0.789 | 0.188 | 0.063 | 0 |
| 44 | MSI1 | POU4F1 | 1556507_at | NA | NA | NA | 0.09 | 0.776 | 0.188 | 0.063 | 0 |
| 43 | MSI1 | POU4F1 | 1556507_at | LCE1E | NA | NA | 0.091 | 0.789 | 0.188 | 0.063 | 0 |
| 41 | LCE1E | POU4F1 | MSI1 | NA | NA | NA | 0.092 | 0.791 | 0.188 | 0.063 | 0 |

TABLE 17

Realtime RT-PCR data of patients with lymphocytic myocarditis (n = 10) vs idiopathic dilated cardiomyopathy (n = 10).

| Probe Set | Gene Symbol | Fold Change by SAM | Fold Change by qPCR | $P < 0.05$ by SAM | $P < 0.05$ by qPCR |
|---|---|---|---|---|---|
| 201721_s_at | CD14 | +5.9 | +6.8 | Y | Y |
| 1554899_s_at | FCER1G | +5.3 | +5 | Y | Y |
| 210146_x_at | TLR1 | +4.5 | +4.2 | Y | Y |
| 204923_at | TLR2 | +3.9 | +5.9 | Y | Y |
| 1555349_a_at | ITGB2 | +3.1 | +1.95 | Y | Y |
| 44673_at | SIGLEC1 | +2.3 | +4.3 | Y | Y |
| 219938_s_at | TLR7 | +2.3 | +2.8 | Y | Y |
| 203741_s_at | ADCY7 | +2 | +4.2 | Y | Y |
| 212830_at | MEGF9 | +1.5 | +2.3 | Y | Y |
| 217777_s_at | PTPLAD1 | +1.5 | +1.7 | Y | Y |
| 209307_at | SWAP70 | +1.4 | +2.1 | Y | Y |
| 206333_at | MSI1 | −1.8 | −8.4 | Y | Y |
| 1559224_at | LCE1E | −2.3 | −2.6 | Y | Y |

TABLE 18

Identification of subtypes of inflammatory cardiomyopathy vs IDCM.

| Subtype | Transriptomic biomarker (number of genes) | Sensitivity (%, 95CI) | Specificity (%, 95CI) | PPV (%, 95CI) | NPV (%, 95CI) | Overall accuracy (%) |
|---|---|---|---|---|---|---|
| Giant cell myocarditis | 8 | 67(13-98) | 92(62-100) | 67(13-98) | 92(62-100) | 86 |
| Sarcoidosis | 58 | 89(51-99) | 67(35-89) | 67(35-89) | 39(51-99) | 77 |
| Peripartum cardiomyopathy | 56 | 83(36-99) | 67(35-89) | 56(23-85) | 89(51-99) | 74 |
| Systemic lupus erythematosus | 21 | 50(9-91) | 100(71-100) | 100(20-100) | 87(58-98) | 76 |

TABLE 19

Classifier to distinguish rare subtypes of inflammatory cardiomyopathy from lymphocytic myocarditis.

| Subtype | Transriptomic biomarker (number of genes) | Sensitivity (%, 95CI) | Specificity (%, 95CI) | PPV (%, 95CI) | NPV (%, 95CI) | Overall accuracy (%) |
|---|---|---|---|---|---|---|
| Giant cell myocarditis | 4 | 100(31-100) | 100(82-100) | 100(31-100) | 100(82-100) | 100 |
| Sarcoidosis | 6 | 100(63-100) | 100(82-100) | 100(63-100) | 100(82-100) | 100 |
| Peripartum cardiomyopathy | 12 | 100(52-100) | 100(82-100) | 100(52-100) | 100(82-100) | 100 |
| Systemic lupus erythematosus | 27 | 25(1-78) | 91(70-98) | 33(2-87) | 88(67-97) | 81 |

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the Disclosure is provided to allow the reader to quickly ascertain the nature of the technical disclosure. It is submitted with the understanding that it will not be used to interpret or limit the scope or meaning of the following claims.

What is claimed is:

1. A method of treating a patient with myocarditis comprising:
   obtaining an endomyocardial biopsy sample from the patient;
   measuring the expression of a set of genes in the sample;
   creating a patient relative gene expression profile, wherein the relative gene expression profile consists of the relative expression of the set of genes: ITGB2, LCE1E, ADCY7, MSI1, SWAP70, MEGF9, PTPLAD1, SIGLEC1, CD14, TLR1, FCER1G, TLR2, and TLR7; and
   comparing the patient relative gene expression profile to a reference relative gene expression profile generated from subjects without myocarditis,
   wherein the patient is identified as having myocarditis when ITGB2, ADCY7, MSI1, SWAP70, MEGF9, PTPLAD1, SIGLEC1, CD14, TLR1, FCER1G, TLR2, and TLR7 have increased expression and LCE1E has decreased expression in the patient relative gene expression profile compared to the reference relative gene expression profile, and
   treating the patient identified as having myocarditis with an anti-inflammatory cytokine, an anti-viral agent, a Ca-channel blocker, or immunoabsorption.

2. The method of claim 1, wherein the patient has symptoms of heart failure.

3. The method of claim 2, wherein the method differentiates whether the patient has myocarditis or idiopathic dilated cardiomyopathy.

4. The method of claim 1, wherein the myocarditis is borderline myocarditis.

5. The method of claim 1, wherein the myocarditis is active myocarditis.

6. The method of claim 1, wherein the expression of the set of genes is measured on a biochip.

7. The method of claim 1, wherein the expression of the set of genes is measured by PCR.

8. The method of claim 1, wherein measuring the expression of a set of genes in the sample comprises, contacting primers that can hybridize to each gene in the set of genes within the sample.

9. The method of claim 8, wherein the expression is measured by PCR.

10. The method of claim 1, wherein measuring the expression of a set of genes in the sample comprises, contacting probes that can hybridize to each gene in the set of genes within the sample.

11. The method of claim 10, wherein the expression is measured by a biochip.

12. The method of claim 1, wherein the patient identified as having myocarditis is treated with interferon (IFN).

13. A method of treating a patient with myocarditis comprising:
    obtaining an endomyocardial biopsy sample from the patient;
    measuring the expression of a set of genes in the sample;
    creating a patient-gene expression profile, wherein the gene expression profile consists of the expression of the set of genes: ITGB2, LCE1E, ADCY7, MSI1, SWAP70, MEGF9, PTPLAD1, SIGLECI, CD14, TLR1, FCER1G, TLR2, and TLR7;
    normalizing the patient-gene expression profile; and
    comparing the normalized patient-gene expression profile to a normalized gene expression profile of a control sample from a subject without myocarditis;
    wherein the patient is identified as having myocarditis when ITGB2, ADCY7, MSI1, SWAP70, MEGF9, PTPLAD1, SIGLEC1, CD14, TLR1, FCER1G, TLR2, and TLR7 have increased expression and LCE1E and MSI1 have decreased expression in the normalized patient-gene expression profile compared to their respective genes in the normalized gene expression profile of the control sample; and
    treating the patient identified as having myocarditis with an anti-inflammatory cytokine, an anti-viral agent, a Ca-channel blocker, or immunoabsorption.

14. The method of claim 13, wherein the patient has symptoms of heart failure.

15. The method of claim 13, wherein the method differentiates whether the patient has myocarditis or idiopathic dilated cardiomyopathy.

16. The method of claim 13, wherein the myocarditis is borderline myocarditis.

17. The method of claim 13, wherein the myocarditis is active myocarditis.

18. The method of claim 13, wherein the expression of the set of genes is measured on a biochip.

* * * * *